United States Patent
Hunter et al.

(10) Patent No.: US 8,793,863 B2
(45) Date of Patent: Aug. 5, 2014

(54) METHOD AND APPARATUS FOR FORMING RETAINERS ON A SUTURE

(75) Inventors: William L. Hunter, Vancouver (CA); Robert A. Herrmann, Vancouver (CA); Alexander Naimagon, Richmond (CA)

(73) Assignee: Ethicon, Inc., Somerville, NJ (US)

( * ) Notice: Subject to any disclaimer, the term of this patent is extended or adjusted under 35 U.S.C. 154(b) by 1299 days.

(21) Appl. No.: 12/101,885

(22) Filed: Apr. 11, 2008

(65) Prior Publication Data

US 2009/0012560 A1    Jan. 8, 2009

Related U.S. Application Data

(60) Provisional application No. 60/911,814, filed on Apr. 13, 2007.

(51) Int. Cl.
*A61B 17/04*    (2006.01)
*A61B 17/06*    (2006.01)
*A61B 17/00*    (2006.01)

(52) U.S. Cl.
CPC ....... *A61B 17/06166* (2013.01); *A61B 17/0469* (2013.01); *A61B 2017/06057* (2013.01); *A61B 2017/06176* (2013.01); *A61B 2017/00526* (2013.01)
USPC .............................................. 29/557; 606/228

(58) Field of Classification Search
CPC ............... A61B 17/06166; A61B 2017/06176; A61B 2017/06166
USPC .............. 29/7.1, 7.2, 7.3, 557, 559; 600/228; 606/228
See application file for complete search history.

(56) References Cited

U.S. PATENT DOCUMENTS

| | | |
|---|---|---|
| 709,392 A | 9/1902 | Brown |
| 733,723 A | 7/1903 | Lukens |
| 789,401 A | 5/1905 | Acheson |
| 816,026 A | 3/1906 | Meier |
| 879,758 A | 2/1908 | Foster |
| 1,142,510 A | 6/1915 | Engle |
| 1,248,825 A | 12/1917 | Dederrer |
| 1,321,011 A | 11/1919 | Cottes |
| 1,558,037 A | 10/1925 | Morton |

(Continued)

FOREIGN PATENT DOCUMENTS

| | | |
|---|---|---|
| BE | 1014364 | 9/2003 |
| CA | 2309844 | 12/1996 |

(Continued)

OTHER PUBLICATIONS

Bellin et al., "Polymeric triple-shape materials", Proceedings of the National Academy of Sciences of the United States of America Nov. 28, 2006; 2103(48):18043-18047.

(Continued)

*Primary Examiner* — Jermie Cozart

(57) ABSTRACT

A method of forming retainers on a suture includes providing a suture having a longitudinal axis and a circumference, a cutter, and a displacer that can longitudinally displace at least one of the suture and the cutter relative to the other, and can at least one of revolve the cutter about the suture and rotate the suture; and placing the cutter and suture into cutting engagement to form a first helical escarpment about the suture circumference. An apparatus for performing the method is also provided.

28 Claims, 21 Drawing Sheets

(56) References Cited

U.S. PATENT DOCUMENTS

| | | |
|---|---|---|
| 1,728,316 A | 9/1929 | Wachenfeldt |
| 1,886,721 A | 11/1932 | O'Brien |
| 2,094,578 A | 10/1937 | Blumenthal et al. |
| 2,201,610 A | 5/1940 | Dawson |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,684,070 A | 7/1954 | Kelsey |
| 2,736,964 A | 3/1956 | Lieberman |
| 2,779,083 A | 1/1957 | Eaton |
| 2,814,296 A | 11/1957 | Everett |
| 2,817,339 A | 12/1957 | Sullivan |
| 2,830,366 A | 4/1958 | Chisena |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski |
| 3,066,452 A * | 12/1962 | Bott et al. ................. 451/28 |
| 3,066,673 A * | 12/1962 | Bott et al. ................. 606/228 |
| 3,068,869 A | 12/1962 | Shelden |
| 3,068,870 A | 12/1962 | Levin |
| 3,082,523 A | 3/1963 | Modes et al. |
| 3,123,077 A | 3/1964 | Alcamo |
| 3,166,072 A | 1/1965 | Sullivan |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling et al. |
| 3,385,299 A | 5/1968 | Le Roy |
| 3,394,704 A | 7/1968 | Dery |
| 3,494,006 A | 2/1970 | Brumlik |
| 3,522,637 A | 8/1970 | Brumlik |
| 3,525,340 A | 8/1970 | Gilbert |
| 3,527,223 A | 9/1970 | Shein |
| 3,545,608 A | 12/1970 | Berger et al. |
| 3,557,795 A | 1/1971 | Hirsch |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | de Mestral et al. |
| 3,748,701 A | 7/1973 | De Mestral |
| 3,762,418 A | 10/1973 | Wasson |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,951,261 A | 4/1976 | Mandel et al. |
| 3,963,031 A | 6/1976 | Hunter |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen et al. |
| 3,987,797 A | 10/1976 | Stephenson |
| 3,990,144 A | 11/1976 | Schwartz |
| 4,006,747 A | 2/1977 | Kronenthal et al. |
| 4,008,303 A | 2/1977 | Glick et al. |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn et al. |
| 4,313,448 A | 2/1982 | Stokes |
| 4,316,469 A | 2/1982 | Kapitanov |
| 4,317,451 A | 3/1982 | Cerwin et al. |
| 4,345,362 A | 8/1982 | de Givry |
| 4,372,293 A | 2/1983 | Vijil-Rosales |
| 4,428,376 A | 1/1984 | Mericle et al. |
| 4,430,998 A | 2/1984 | Harvey et al. |
| 4,434,796 A | 3/1984 | Karapetian et al. |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows et al. |
| 4,741,330 A | 5/1988 | Hayhurst |
| 4,750,910 A | 6/1988 | Takayanagi et al. |
| 4,751,621 A | 6/1988 | Jenkins |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuk et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schutz et al. |
| 4,950,258 A | 8/1990 | Kawai et al. |
| 4,950,285 A | 8/1990 | Wilk |
| 4,968,315 A | 11/1990 | Gatturna et al. |
| 4,976,715 A | 12/1990 | Bays et al. |
| 4,979,956 A | 12/1990 | Silvestrini et al. |
| 4,981,149 A | 1/1991 | Yoon et al. |
| 4,994,073 A | 2/1991 | Green |

(56) References Cited

U.S. PATENT DOCUMENTS

| | | |
|---|---|---|
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson et al. |
| 5,102,418 A | 4/1992 | Granger et al. |
| 5,102,421 A | 4/1992 | Anspach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,234,006 A | 8/1993 | Eaton et al. |
| 5,242,457 A | 9/1993 | Akopov et al. |
| 5,246,441 A | 9/1993 | Ross et al. |
| 5,249,673 A | 10/1993 | Sinn |
| 5,258,013 A | 11/1993 | Granger et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green et al. |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,336,239 A | 8/1994 | Gimpelson |
| 5,341,922 A | 8/1994 | Cerwin et al. |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,391,173 A | 2/1995 | Wilk |
| 5,395,126 A | 3/1995 | Tresslar |
| 5,403,346 A | 4/1995 | Loeser |
| 5,411,523 A | 5/1995 | Goble |
| 5,414,988 A | 5/1995 | Dipalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,494,154 A | 2/1996 | Ainsworth et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch et al. |
| 5,522,845 A | 6/1996 | Wenstrom, Jr. et al. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,533,982 A | 7/1996 | Rizk et al. |
| 5,536,582 A | 7/1996 | Prasad et al. |
| 5,540,705 A | 7/1996 | Meade et al. |
| 5,540,718 A | 7/1996 | Bartlett |
| 5,546,957 A | 8/1996 | Heske |
| 5,549,631 A | 8/1996 | Bonutti |
| 5,554,171 A | 9/1996 | Gatturna et al. |
| 5,566,822 A | 10/1996 | Scanlon |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup III, et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,714 A | 9/1997 | Charvin et al. |
| 5,669,935 A | 9/1997 | Rosenman et al. |
| 5,676,675 A | 10/1997 | Grice |
| D386,583 S | 11/1997 | Ferragamo et al. |
| 5,683,417 A | 11/1997 | Cooper |
| D387,161 S | 12/1997 | Ferragamo et al. |
| 5,693,072 A | 12/1997 | McIntosh |
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans |
| 5,731,855 A | 3/1998 | Koyama et al. |
| 5,741,277 A | 4/1998 | Gordon et al. |
| 5,744,151 A | 4/1998 | Capelli |
| 5,763,411 A | 6/1998 | Edwardson et al. |
| 5,765,560 A | 6/1998 | Verkerke et al. |
| 5,766,246 A | 6/1998 | Mulhauser et al. |

(56) References Cited

U.S. PATENT DOCUMENTS

| | | | |
|---|---|---|---|
| 5,779,719 A | 7/1998 | Klein et al. |
| 5,782,864 A | 7/1998 | Lizardi |
| 5,807,403 A | 9/1998 | Beyar et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,884,859 A | 3/1999 | Ma |
| 5,887,594 A | 3/1999 | Locicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,921,982 A | 7/1999 | Lesh et al. |
| 5,925,078 A | 7/1999 | Anderson |
| 5,931,855 A | 8/1999 | Buncke |
| 5,935,138 A | 8/1999 | McJames, II et al. |
| 5,938,668 A | 8/1999 | Scirica et al. |
| 5,941,899 A | 8/1999 | Granger et al. |
| 5,950,505 A | 9/1999 | Locher |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 5,320,629 B1 | 5/2000 | Noda et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 * | 2/2001 | Labrecque et al. ............ 118/110 |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,463,719 B2 | 10/2002 | Dey et al. |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,645,228 B2 | 11/2003 | Renz |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,702,844 B1 | 3/2004 | Lazarus |
| 6,712,830 B2 | 3/2004 | Esplin |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,773,450 B2 | 8/2004 | Leung et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Lendlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs et al. |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,921,811 B2 | 7/2005 | Zamora et al. |
| 6,923,819 B2 | 8/2005 | Meade et al. |
| 6,945,021 B2 | 9/2005 | Michel |

(56) References Cited

U.S. PATENT DOCUMENTS

| | | |
|---|---|---|
| 6,945,980 B2 | 9/2005 | Nguyen et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson et al. |
| 7,037,984 B2 | 5/2006 | Lendlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,081,135 B2 | 7/2006 | Smith et al. |
| 7,083,637 B1 | 8/2006 | Tannhauser |
| 7,083,648 B2 | 8/2006 | Yu et al. |
| 7,107,090 B2 | 9/2006 | Salisbury, Jr. et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,757 B2 | 12/2006 | Fallin et al. |
| 7,156,858 B2 | 1/2007 | Schuldt-Hempe et al. |
| 7,156,862 B2 | 1/2007 | Jacobs et al. |
| 7,160,312 B2 | 1/2007 | Saadat |
| 7,166,570 B2 | 1/2007 | Hunter et al. |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmielding et al. |
| 7,211,088 B2 | 5/2007 | Grafton et al |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,297,142 B2 | 11/2007 | Brock |
| 7,322,105 B2 | 1/2008 | Lewis |
| 7,371,253 B2 | 5/2008 | Leung et al. |
| 7,513,904 B2 | 4/2009 | Sulamanidze et al. |
| 7,514,095 B2 | 4/2009 | Nelson et al. |
| 7,582,105 B2 | 9/2009 | Kolster |
| 7,601,164 B2 | 10/2009 | Wu |
| 7,624,487 B2 | 12/2009 | Trull et al. |
| 7,645,293 B2 | 1/2010 | Martinek et al. |
| 7,806,908 B2 | 10/2010 | Ruff |
| 7,845,356 B2 | 12/2010 | Paraschac et al. |
| 7,857,829 B2 | 12/2010 | Kaplan et al. |
| 7,879,072 B2 | 2/2011 | Bonutti et al. |
| 7,913,365 B2 | 3/2011 | Genova et al. |
| 7,919,112 B2 | 4/2011 | Pathak et al. |
| 7,996,967 B2 | 8/2011 | Genova et al. |
| 7,996,968 B2 | 8/2011 | Genova et al. |
| 8,011,072 B2 | 9/2011 | Genova et al. |
| 8,015,678 B2 | 9/2011 | Genova |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,118,834 B1 | 2/2012 | Goraltchouk et al. |
| 8,216,273 B1 | 7/2012 | Goraltchouk et al. |
| 8,226,684 B2 | 7/2012 | Nawrocki et al. |
| 8,308,761 B2 | 11/2012 | Brailovski et al. |
| 8,615,856 B1 | 12/2013 | Gelbart |
| 2001/0011187 A1 | 8/2001 | Pavcnik et al. |
| 2001/0018592 A1 | 8/2001 | Schaller et al. |
| 2001/0018599 A1 | 8/2001 | D'Aversa et al. |
| 2001/0039450 A1 | 11/2001 | Pavcnik et al. |
| 2001/0044637 A1 | 11/2001 | Jacobs et al. |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0069617 A1 | 6/2002 | Dey et al. |
| 2002/0077448 A1 | 6/2002 | Antal et al. |
| 2002/0077631 A1 | 6/2002 | Lubbers et al. |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0138009 A1 | 9/2002 | Brockway et al. |
| 2002/0151932 A1 | 10/2002 | Bryant et al. |
| 2002/0151980 A1 | 10/2002 | Cauthen |
| 2002/0161168 A1 | 10/2002 | Shalaby et al. |
| 2002/0173807 A1 | 11/2002 | Jacobs |
| 2002/0173822 A1 | 11/2002 | Justin et al. |
| 2002/0179718 A1 | 12/2002 | Murokh et al. |
| 2003/0014077 A1 | 1/2003 | Leung et al. |
| 2003/0040795 A1 | 2/2003 | Elson et al. |
| 2003/0041426 A1 | 3/2003 | Genova et al. |
| 2003/0065360 A1 | 4/2003 | Jacobs et al. |
| 2003/0065402 A1 | 4/2003 | Anderson et al. |
| 2003/0069602 A1 | 4/2003 | Jacobs et al. |
| 2003/0074021 A1 | 4/2003 | Morriss et al. |
| 2003/0074023 A1 | 4/2003 | Kaplan et al. |
| 2003/0078604 A1 | 4/2003 | Walshe |
| 2003/0088270 A1 | 5/2003 | Lubbers et al. |
| 2003/0097150 A1 | 5/2003 | Fallin et al. |
| 2003/0105489 A1 | 6/2003 | Eichhorn et al. |
| 2003/0149447 A1 | 8/2003 | Morency et al. |
| 2003/0158604 A1 | 8/2003 | Cauthen, III et al. |
| 2003/0167072 A1 | 9/2003 | Oberlander |
| 2003/0199923 A1 | 10/2003 | Khairkhahan et al. |
| 2003/0203003 A1 | 10/2003 | Nelson et al. |
| 2003/0204193 A1 | 10/2003 | Gabriel et al. |
| 2003/0204195 A1 | 10/2003 | Keane et al. |
| 2003/0225424 A1 | 12/2003 | Benderev |
| 2003/0229361 A1 | 12/2003 | Jackson |
| 2003/0236550 A1 | 12/2003 | Peterson et al. |
| 2003/0236551 A1 | 12/2003 | Peterson |
| 2004/0006353 A1 | 1/2004 | Bosley, Jr. et al. |
| 2004/0010275 A1 | 1/2004 | Jacobs et al. |
| 2004/0010276 A1 | 1/2004 | Jacobs et al. |
| 2004/0015187 A1 | 1/2004 | Lendlein et al. |
| 2004/0024169 A1 | 2/2004 | Shalaby et al. |
| 2004/0024420 A1 | 2/2004 | Lubbers et al. |
| 2004/0028655 A1 | 2/2004 | Nelson et al. |
| 2004/0030354 A1 | 2/2004 | Leung et al. |
| 2004/0039415 A1 | 2/2004 | Zamierowski |
| 2004/0049224 A1 | 3/2004 | Buehlmann et al. |
| 2004/0059370 A1 | 3/2004 | Greene, Jr. et al. |
| 2004/0059377 A1 | 3/2004 | Peterson et al. |
| 2004/0059378 A1 | 3/2004 | Peterson et al. |
| 2004/0060409 A1 | 4/2004 | Leung et al. |
| 2004/0060410 A1 | 4/2004 | Leung et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0093023 A1 | 5/2004 | Allen et al. |
| 2004/0093028 A1 | 5/2004 | Ruff |
| 2004/0098051 A1 | 5/2004 | Fallin et al. |
| 2004/0106949 A1 | 6/2004 | Cohn et al. |
| 2004/0116620 A1 | 6/2004 | Shalaby et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0167575 A1 | 8/2004 | Roby |
| 2004/0186487 A1 | 9/2004 | Klein et al. |
| 2004/0193191 A1 | 9/2004 | Starksen et al. |

(56) References Cited

U.S. PATENT DOCUMENTS

| | | |
|---|---|---|
| 2004/0193217 A1 | 9/2004 | Lubbers et al. |
| 2004/0193257 A1 | 9/2004 | Wu et al. |
| 2004/0226427 A1 | 11/2004 | Trull et al. |
| 2004/0230223 A1 | 11/2004 | Bonutti et al. |
| 2004/0237736 A1* | 12/2004 | Genova et al. .................... 83/13 |
| 2004/0254609 A1 | 12/2004 | Esplin |
| 2004/0260340 A1 | 12/2004 | Jacobs et al. |
| 2004/0265282 A1 | 12/2004 | Wright et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0033367 A1 | 2/2005 | Leung et al. |
| 2005/0034431 A1 | 2/2005 | Dey et al. |
| 2005/0038472 A1 | 2/2005 | Furst |
| 2005/0049636 A1 | 3/2005 | Leiboff |
| 2005/0055051 A1 | 3/2005 | Grafton |
| 2005/0059984 A1 | 3/2005 | Chanduszko et al. |
| 2005/0065533 A1 | 3/2005 | Magen et al. |
| 2005/0070959 A1 | 3/2005 | Cichocki, Jr. |
| 2005/0080455 A1 | 4/2005 | Schmieding et al. |
| 2005/0085857 A1 | 4/2005 | Peterson et al. |
| 2005/0096698 A1 | 5/2005 | Lederman |
| 2005/0106211 A1 | 5/2005 | Nelson et al. |
| 2005/0113936 A1 | 5/2005 | Brustad et al. |
| 2005/0119694 A1 | 6/2005 | Jacobs et al. |
| 2005/0125020 A1 | 6/2005 | Meade et al. |
| 2005/0125034 A1 | 6/2005 | Cichocki, Jr. |
| 2005/0125035 A1 | 6/2005 | Cichocki, Jr. |
| 2005/0149064 A1 | 7/2005 | Peterson et al. |
| 2005/0149118 A1 | 7/2005 | Koyfman et al. |
| 2005/0154255 A1 | 7/2005 | Jacobs |
| 2005/0171561 A1 | 8/2005 | Songer et al. |
| 2005/0177190 A1 | 8/2005 | Zamierowski |
| 2005/0181009 A1 | 8/2005 | Hunter et al. |
| 2005/0182444 A1 | 8/2005 | Peterson et al. |
| 2005/0182445 A1 | 8/2005 | Zamierowski |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0234510 A1 | 10/2005 | Zamierowski |
| 2005/0240220 A1 | 10/2005 | Zamierowski |
| 2005/0240224 A1 | 10/2005 | Wu |
| 2005/0267531 A1 | 12/2005 | Ruff et al. |
| 2005/0267532 A1 | 12/2005 | Wu |
| 2005/0277984 A1 | 12/2005 | Long |
| 2005/0283246 A1 | 12/2005 | Cauthen et al. |
| 2006/0020272 A1 | 1/2006 | Gildenberg |
| 2006/0030884 A1 | 2/2006 | Yeung et al. |
| 2006/0036266 A1 | 2/2006 | Sulamanidze et al. |
| 2006/0058470 A1 | 3/2006 | Rizk |
| 2006/0058574 A1 | 3/2006 | Priewe et al. |
| 2006/0058799 A1 | 3/2006 | Elson et al. |
| 2006/0058844 A1 | 3/2006 | White et al. |
| 2006/0063476 A1 | 3/2006 | Dore |
| 2006/0064115 A1 | 3/2006 | Allen et al. |
| 2006/0064116 A1 | 3/2006 | Allen et al. |
| 2006/0064127 A1 | 3/2006 | Fallin et al. |
| 2006/0079469 A1 | 4/2006 | Anderson et al. |
| 2006/0079935 A1 | 4/2006 | Kolster |
| 2006/0085016 A1 | 4/2006 | Eremia |
| 2006/0089525 A1 | 4/2006 | Mamo et al. |
| 2006/0089672 A1 | 4/2006 | Martinek |
| 2006/0111734 A1 | 5/2006 | Kaplan et al. |
| 2006/0111742 A1 | 5/2006 | Kaplan et al. |
| 2006/0116503 A1 | 6/2006 | Lendlein et al. |
| 2006/0122608 A1 | 6/2006 | Fallin et al. |
| 2006/0135994 A1 | 6/2006 | Ruff et al. |
| 2006/0135995 A1 | 6/2006 | Ruff et al. |
| 2006/0140999 A1 | 6/2006 | Lendlein et al. |
| 2006/0142784 A1 | 6/2006 | Kontos |
| 2006/0193769 A1 | 8/2006 | Nelson et al. |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235445 A1 | 10/2006 | Birk et al. |
| 2006/0235447 A1 | 10/2006 | Walshe |
| 2006/0235516 A1 | 10/2006 | Cavazzoni |
| 2006/0241658 A1 | 10/2006 | Cerundolo |
| 2006/0249405 A1 | 11/2006 | Cerwin et al. |
| 2006/0253126 A1 | 11/2006 | Bjerken et al. |
| 2006/0257629 A1 | 11/2006 | Lendlein et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0282099 A1 | 12/2006 | Stokes et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2006/0293710 A1 | 12/2006 | Foerster et al. |
| 2007/0005109 A1 | 1/2007 | Popadiuk et al. |
| 2007/0005110 A1 | 1/2007 | Collier et al. |
| 2007/0016251 A1 | 1/2007 | Roby |
| 2007/0021779 A1 | 1/2007 | Garvin et al. |
| 2007/0027475 A1 | 2/2007 | Pagedas |
| 2007/0038249 A1 | 2/2007 | Kolster |
| 2007/0065663 A1 | 3/2007 | Trull et al. |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0135843 A1 | 6/2007 | Burkhart |
| 2007/0151961 A1 | 7/2007 | Kleine et al. |
| 2007/0156175 A1 | 7/2007 | Weadock et al. |
| 2007/0167958 A1 | 7/2007 | Sulamanidze et al. |
| 2007/0187861 A1 | 8/2007 | Genova et al. |
| 2007/0208355 A1 | 9/2007 | Ruff |
| 2007/0208377 A1 | 9/2007 | Kaplan et al. |
| 2007/0213770 A1 | 9/2007 | Dreyfuss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0227914 A1 | 10/2007 | Cerwin et al. |
| 2007/0233188 A1 | 10/2007 | Hunt et al. |
| 2007/0239206 A1 | 10/2007 | Shelton, IV et al. |
| 2007/0239207 A1 | 10/2007 | Beramendi |
| 2007/0257395 A1 | 11/2007 | Lindh et al. |
| 2007/0282247 A1 | 12/2007 | Desai et al. |
| 2007/0293892 A1 | 12/2007 | Takasu |
| 2008/0004490 A1 | 1/2008 | Bosley, Jr. et al. |
| 2008/0004603 A1 | 1/2008 | Larkin et al. |
| 2008/0009838 A1 | 1/2008 | Schena et al. |
| 2008/0009888 A1 | 1/2008 | Ewers et al. |
| 2008/0009902 A1 | 1/2008 | Hunter et al. |
| 2008/0027273 A1 | 1/2008 | Gutterman |
| 2008/0027486 A1 | 1/2008 | Jones et al. |
| 2008/0046094 A1 | 2/2008 | Han et al. |
| 2008/0058869 A1 | 3/2008 | Stopek et al. |
| 2008/0064839 A1 | 3/2008 | Hadba et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0109036 A1 | 5/2008 | Stopek et al. |
| 2008/0131692 A1 | 6/2008 | Rolland et al. |
| 2008/0132943 A1 | 6/2008 | Maiorino et al. |
| 2008/0169059 A1 | 7/2008 | Messersmith et al. |
| 2008/0195147 A1 | 8/2008 | Stopek |
| 2008/0208358 A1 | 8/2008 | Bellamkonda et al. |
| 2008/0215072 A1 | 9/2008 | Kelly |
| 2008/0221618 A1 | 9/2008 | Chen et al. |
| 2008/0234731 A1 | 9/2008 | Leung et al. |
| 2008/0248216 A1 | 10/2008 | Yeung et al. |

(56) References Cited

U.S. PATENT DOCUMENTS

| | | |
|---|---|---|
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2008/0312688 A1 | 12/2008 | Nawrocki et al. |
| 2009/0012560 A1 | 1/2009 | Hunter et al. |
| 2009/0018577 A1 | 1/2009 | Leung et al. |
| 2009/0043336 A1 | 2/2009 | Yuan et al. |
| 2009/0076543 A1 | 3/2009 | Maiorino et al. |
| 2009/0082856 A1 | 3/2009 | Flanagan |
| 2009/0088835 A1 | 4/2009 | Wang |
| 2009/0099597 A1 | 4/2009 | Isse |
| 2009/0105753 A1 | 4/2009 | Greenhalgh et al. |
| 2009/0107965 A1 | 4/2009 | D'Agostino |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0200487 A1 | 8/2009 | Maiorino et al. |
| 2009/0210006 A1 | 8/2009 | Cohen et al. |
| 2009/0216253 A1 | 8/2009 | Bell et al. |
| 2009/0226500 A1 | 9/2009 | Avelar et al. |
| 2009/0248066 A1 | 10/2009 | Wilkie |
| 2009/0248067 A1 | 10/2009 | Maiorino |
| 2009/0248070 A1 | 10/2009 | Kosa et al. |
| 2009/0250356 A1 | 10/2009 | Kirsch et al. |
| 2009/0250588 A1 | 10/2009 | Robeson et al. |
| 2009/0259233 A1 | 10/2009 | Bogart et al. |
| 2009/0259251 A1 | 10/2009 | Cohen |
| 2009/0287245 A1 | 11/2009 | Ostrovsky et al. |
| 2009/0299407 A1 | 12/2009 | Yuan et al. |
| 2009/0299408 A1 | 12/2009 | Schuldt-Hempe et al. |
| 2009/0306710 A1 | 12/2009 | Lindh et al. |
| 2009/0318958 A1 | 12/2009 | Ochiai |
| 2010/0021516 A1 | 1/2010 | McKay |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0071833 A1 | 3/2010 | Maiorino |
| 2010/0087855 A1 | 4/2010 | Leung et al. |
| 2010/0101707 A1 | 4/2010 | Maiorino et al. |
| 2010/0140115 A1 | 6/2010 | Kirsch |
| 2010/0160961 A1 | 6/2010 | Nawrocki et al. |
| 2010/0163056 A1 | 7/2010 | Tschopp et al. |
| 2010/0198257 A1 | 8/2010 | Stopek et al. |
| 2010/0211097 A1 | 8/2010 | Hadba et al. |
| 2010/0211098 A1 | 8/2010 | Hadba et al. |
| 2010/0230300 A1 | 9/2010 | Hunter et al. |
| 2010/0239635 A1 | 9/2010 | McClain et al. |
| 2010/0292718 A1 | 11/2010 | Sholev et al. |
| 2010/0294103 A1 | 11/2010 | Genova et al. |
| 2010/0294104 A1 | 11/2010 | Genova et al. |
| 2010/0294105 A1 | 11/2010 | Genova et al. |
| 2010/0294106 A1 | 11/2010 | Genova et al. |
| 2010/0294107 A1 | 11/2010 | Genova et al. |
| 2010/0298637 A1 | 11/2010 | Ruff |
| 2010/0298639 A1 | 11/2010 | Leung et al. |
| 2010/0298848 A1 | 11/2010 | Leung et al. |
| 2010/0298867 A1 | 11/2010 | Ruff |
| 2010/0298868 A1 | 11/2010 | Ruff |
| 2010/0298871 A1 | 11/2010 | Ruff et al. |
| 2010/0298878 A1 | 11/2010 | Leung et al. |
| 2010/0298879 A1 | 11/2010 | Leung et al. |
| 2010/0298880 A1 | 11/2010 | Leung et al. |
| 2010/0313723 A1 | 12/2010 | Genova et al. |
| 2010/0313729 A1 | 12/2010 | Genova et al. |
| 2010/0313730 A1 | 12/2010 | Genova et al. |
| 2010/0318122 A1 | 12/2010 | Leung et al. |
| 2010/0318123 A1 | 12/2010 | Leung et al. |
| 2010/0318124 A1 | 12/2010 | Leung et al. |
| 2011/0009902 A1 | 1/2011 | Leung et al. |
| 2011/0046669 A1 | 2/2011 | Goraltchouk et al. |
| 2011/0093010 A1 | 4/2011 | Genova et al. |
| 2011/0106152 A1 | 5/2011 | Kozlowski |
| 2011/0130774 A1 | 6/2011 | Criscuolo et al. |
| 2011/0166597 A1 | 7/2011 | Herrmann et al. |
| 2012/0109188 A1 | 5/2012 | Viola |

FOREIGN PATENT DOCUMENTS

| | | |
|---|---|---|
| CN | 2640420 | 9/2004 |
| DE | P 1 810 800 | 6/1970 |
| DE | 03227984 | 2/1984 |
| DE | 43 02 895 | 8/1994 |
| DE | 19618891 | 4/1997 |
| DE | 19833703 | 2/2000 |
| DE | 10245025 | 4/2004 |
| DE | 10 2005 004317 | 6/2006 |
| EP | 0121362 | 9/1987 |
| EP | 0329787 | 8/1989 |
| EP | 0428253 | 5/1991 |
| EP | 0464479 | 1/1992 |
| EP | 0513713 | 5/1992 |
| EP | 0513736 | 11/1992 |
| EP | 0558993 | 9/1993 |
| EP | 0574707 | 12/1993 |
| EP | 0576337 | 12/1993 |
| EP | 0612504 | 8/1994 |
| EP | 0632999 | 1/1995 |
| EP | 0464480 | 3/1995 |
| EP | 0664198 | 7/1995 |
| EP | 0673624 | 9/1995 |
| EP | 0705567 | 4/1996 |
| EP | 0755656 | 1/1997 |
| EP | 0576337 B1 | 3/1997 |
| EP | 826337 | 3/1998 |
| EP | 0913123 | 5/1999 |
| EP | 0916310 | 5/1999 |
| EP | 1075843 | 2/2001 |
| EP | 0839499 | 9/2003 |
| EP | 1525851 | 4/2005 |
| EP | 1532942 | 5/2005 |
| EP | 1 726 317 | 11/2006 |
| EP | 0991359 | 11/2007 |
| EP | 2036502 | 3/2009 |
| EP | 1948261 | 11/2010 |
| EP | 2338421 | 11/2012 |
| FR | 2619129 | 2/1989 |
| FR | 2693108 | 1/1994 |
| FR | 9208059 | 3/1997 |
| GB | 267007 | 3/1927 |
| GB | 1091282 | 11/1967 |
| GB | 1428560 | 7/1973 |
| GB | 1506362 | 4/1978 |
| GB | 1508627 | 4/1978 |
| JP | 1506362 | 4/1978 |
| JP | 054116419 | 9/1979 |
| JP | 63-500702 | 3/1988 |
| JP | 63288146 | 11/1988 |
| JP | 001113091 | 5/1989 |
| JP | 003-165751 | 7/1991 |
| JP | 4-96758 | 3/1992 |
| JP | 4-226642 | 8/1992 |
| JP | 004-266749 | 9/1992 |
| JP | 9-103477 | 4/1997 |
| JP | 10-511009 | 10/1997 |
| JP | 10-503389 | 3/1998 |
| JP | 410085225 | 4/1998 |
| JP | 11-313826 | 11/1999 |
| JP | 011332828 | 12/1999 |
| JP | 2002-59235 | 2/2002 |
| JP | 2002-511308 | 4/2002 |
| JP | 2003-275217 | 9/2003 |
| JP | 2004-530524 | 10/2004 |
| JP | 2005-500119 | 1/2005 |
| JP | 2006-516902 | 7/2006 |
| JP | 2006-517112 | 7/2006 |
| JP | 2009-118967 | 6/2009 |
| KR | 10-2005-0072908 | 7/2005 |
| KR | 6013299 | 2/2006 |
| KR | 2006-59142 | 6/2006 |
| NZ | 501224 | 3/2002 |
| NZ | 531262 | 12/2005 |

(56) References Cited

FOREIGN PATENT DOCUMENTS

| | | |
|---|---|---|
| RU | 2139690 | 7/1992 |
| RU | 2175855 | 11/2001 |
| RU | 2241389 | 12/2004 |
| RU | 2268752 | 1/2006 |
| SU | 1745214 | 8/1992 |
| SU | 1752358 | 10/1999 |
| WO | 86/00020 | 1/1986 |
| WO | 87/01270 | 3/1987 |
| WO | WO 88/09157 | 12/1988 |
| WO | WO 89/05618 | 6/1989 |
| WO | WO 90/09149 | 8/1990 |
| WO | 90/14795 | 12/1990 |
| WO | 92/22336 | 7/1992 |
| WO | 96/06565 | 8/1992 |
| WO | 95/16399 | 6/1995 |
| WO | 95/29637 | 11/1995 |
| WO | WO 9852473 | 11/1998 |
| WO | WO 98/55031 | 12/1998 |
| WO | WO 9921488 | 5/1999 |
| WO | WO 99/33401 | 7/1999 |
| WO | 99/52478 | 10/1999 |
| WO | 99/59477 | 11/1999 |
| WO | 0960600 | 12/1999 |
| WO | WO 99/62431 | 12/1999 |
| WO | 00/51685 | 9/2000 |
| WO | WO 00/51658 | 9/2000 |
| WO | WO 01/06952 | 2/2001 |
| WO | 01/56626 | 8/2001 |
| WO | 03/003925 | 1/2003 |
| WO | WO 03/001979 | 1/2003 |
| WO | WO 03/017850 | 3/2003 |
| WO | WO 03/045255 | 6/2003 |
| WO | WO 03/077772 | 9/2003 |
| WO | WO 03/092758 | 11/2003 |
| WO | 03/103733 | 12/2003 |
| WO | WO 03/103972 | 12/2003 |
| WO | WO 03/105703 | 12/2003 |
| WO | 2004/014236 | 2/2004 |
| WO | 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | 2004/100801 | 11/2004 |
| WO | WO 2004/112853 | 12/2004 |
| WO | 2005/016176 | 2/2005 |
| WO | 2005/074913 | 8/2005 |
| WO | WO 2005/096955 | 10/2005 |
| WO | WO 2005/096956 | 10/2005 |
| WO | 2005/112787 | 12/2005 |
| WO | WO 2006/005144 | 1/2006 |
| WO | WO 2006/012128 | 2/2006 |
| WO | 2006/037399 | 4/2006 |
| WO | WO 2006/061868 | 6/2006 |
| WO | 2006/082060 | 8/2006 |
| WO | WO 2006/079469 | 8/2006 |
| WO | WO 2006/099703 | 9/2006 |
| WO | 2006/138300 | 12/2006 |
| WO | WO 2007/005291 | 1/2007 |
| WO | WO 2007005296 | 1/2007 |
| WO | 2007/038837 | 4/2007 |
| WO | WO 2007/053812 | 5/2007 |
| WO | 2007/089864 | 8/2007 |
| WO | WO 2007/112024 | 10/2007 |
| WO | WO 2007/133103 | 11/2007 |
| WO | 2007/145614 | 12/2007 |
| WO | 2008/128113 | 10/2008 |
| WO | 2009/042841 | 4/2009 |
| WO | 2009/068252 | 6/2009 |
| WO | 2009/087105 | 7/2009 |
| WO | 2009/097556 | 8/2009 |
| WO | 2009/151876 | 12/2009 |
| WO | 2010/052007 | 5/2010 |
| WO | 2011/053375 | 5/2011 |
| WO | 2011/139916 | 11/2011 |
| WO | 2011/140283 | 11/2011 |

OTHER PUBLICATIONS

Bunnell, S., "Gig pull-out suture for tendons." J Bone Joint Surg Am. Jul. 1954;36-A(4):850-1.

Dattillo, Jr., Philip Paul, "Knotless Bi-directional Barbed Absorbable Surgical Suture", Dissertation submitted to the Graduate Faculty of North Carolina State University Textile Management and Technology Nov. 2002, 75 pages.

Delorenzi, C.L., "Barbed Sutures: Rationale and Technique." Aesthetic Surg J. Mar. 2006 26(2): 223-229.

Han, Hongtao et al., "Mating and Piercing Micromechanical Structures for Surface Bonding Applications", Proceedings of the 1991 Micro Electro Mechanical Systems (MEMS '91), An Investigation of Micro Structures, Sensors, Actuators, Machines and Robots, Feb. 1991, pp. 253-258.

Ingle, Nilesh P et al., "Barbed Suture Anchoring Strength: Applicability to Dissimilar Polymeric Materials", College of Textiles, North Carolina State University, 7$^{th}$ World Biomaterials Congress 2004, 1 page.

Ingle, Nilesh P et al., "Testing the Tissue-holding Capacity of Barbed Sutures", College of Textiles, North Carolina State University, Fiber Science—The Next Generation Oct. 17-19, 2005, New Jersey Institute of Technology, Newark, NJ, 4 pages.

International Search Report for PCT/US2007/074658 dated Jun. 12, 2007, 4 pages.

International Search Report for PCT/US2008/060127 dated Sep. 23, 2008, 8 pages.

International Search Report for PCT/US2008/0064921 dated Nov. 19, 2008, 8 pages.

International Search Report for PCT/US2008/075849 dated Mar. 18, 2009, 7 pages.

Jennings et al., "A new technique in primary tendon repair." Surg Gynecol Obstet Nov. 1952;95(5):597-600.

Kaminer, M. et al., "ContourLift™:A New Method of Minimally Invasive Facial Rejuvenation", Cosmetic Dermatology Jan. 2007; 20(1): 29-35.

Kelch et al., "Shape-memory Polymer Networks from Olio[(ϵ-hydroxycaproate)-co-glycolate]dimethacrylates and Butyl Acrylate with Adjustable Hydrolytic Degradation Rate", Biomacromolecules 2007;8(3):1018-1027.

Leung, J. et al., "Performance Enhancement of a Knotless Suture via Barb Geometry Modifications", 7$^{th}$ World Biomaterials Congress 2004, 1 page.

Leung, J. et al., "Barbed, Bi-directional Medical Sutures: Biomechanical Properties and Wound Closure Efficacy Study", 2002 Society for Biomaterials 28$^{th}$ Annual Meeting Transactions, 1 page.

Maitland et al., "Prototype laser-activated shape memory polymer foam device for embolic treatment of aneurysms", Journal of Biomedical Optics May/Jun. 2007;12(3): pp. 030504-1 to 030504-3.

Malina, M. et al., "Endovascular AAA Exclusion: Will Stents With Hooks and Barbs Prevent Stent-Graft Migration?", Journal of Endovascular Surgery 1998; 5; 310-317.

Mansberger, et al., "A New Type Pull-Out Wire for Tendon Surgery: A Preliminary Report", Department of Surgery, University Hospital and University of Maryland School of Medicine, Baltimore, Maryland, Received for Publication May 10, 1951, pp. 119-121.

Mason, M.L., "Primary and secondary tendon suture. A discussion of the significance of technique in tendon surgery." Surg Gynecol Obstet 70 (1940).

McKee, G.K., "Metal anastomosis tubes in tendon suture." The Lancet, May 26, 1945, 659-660.

McKenzie, A.R."An Experimental Multiple Barbed Suture for the Long Flexor Tendons of the Palm and Fingers." J Bone Joint Surg. 49B-(3): 440, Aug. 3, 1967.

Moran et al., "Bidirectional-Barbed Sutured Knotless Running Anastomosis v Classic van Velthovan in a Model System", Journal of Endourology Oct. 2007; 21(10); 1175-1177.

(56) References Cited

OTHER PUBLICATIONS

Murtha et al., "Evaluation of a Novel Technique for Wound Closure Using a Barbed Suture", Journal of the American Society of Plastic Surgeons 2006; 117(6); 1769-1780.
Paul, Malcolm, "Using Barbed Sutures in Open/Subperiosteal Midface Lifting", Aesthetic Surgery Journal Nov./Dec. 2006; 26(6):725-732.
Potenza, Austin, "Tendon Healing Within the Flexor Digital Sheath in the Dog: An Experimental Study", Journal of Bone & Joint Surgery Jan. 1962; 44A(1):49-64.
Pulvertaft, "Suture Materials and Tendon Junctures", American Journal of Surgery Mar. 1965; 109:346-352.
Rodeheaver, G.T. et al., "Barbed Sutures for Wound Closure: In Vivo Wound Security, Tissue Compatibility and Cosmesis Measurements", Society for Biomaterials $30^{th}$ Annual Meeting Transactions, 2 pages.
Ruff, Gregory, "Technique and Uses for Absorbable Barbed Sutures", Aesthetic Surgery Journal Sep./Oct. 2006; 26:620-628.
Singapore Search Report for Singapore Patent Application No. 200702625-5 dated Nov. 26, 2008, 8 pages.
Singapore Search Report for Singapore Patent Application No. 200702350-0 dated Nov. 26, 2008, 7 pages.
Singapore Search Report for Singapore Patent Application No. 200703688-2 dated Nov. 26, 2008, 8 pages.
Sulamanidze, MD, M.A., et al., "Removal of Facial Soft Tissue Ptosis with Special Threads." Dermatol Surg 2002; 28; pp. 367-371.
Szarmach, Robin et al., "An Expanded Surgical Suture and Needle Evaulation and Selection Program by a Healthcare Resource Management Group Purchasing Organization", Journal of Long-Term Effects of Medical Implants 2003; 13(3); 155-170.
Verdan, Claude, "Primary Repair of Flexor Tendons", Journal of Bone and Joint Surgery Jun. 1960; 42(4):647-657.
US 6,447,535, (withdrawn).
US 6,503,260, (withdrawn).
Bacci, Pier Antonio, "Chirurgia Estetica Mini Invasiva Con Fili di Sostegno", Collana di Arti, Pensiero e Scienza; Minelli Editore—2006; 54 pgs.
Behl, Marc et al., "Shape-Memory Polymers", Materials Today Apr. 2007; 10(4); 20-28.
Belkas, J. S. et al., "Peripheral nerve regeneration through a synthetic hydrogel nerve tube", Restorative Neurology and Neuroscience 23 (2005) 19-29.
Boenisch, U.W. et al 'Pull-Out strength and stiffness of meniscal repair using absorbable arrows or Ti-Cron vertical and horizontal loop sutures' American Journal of Sports Medicine, Sep.-Oct. (1999) vol. 27, Issue 5, pp. 626-631.
Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.
Buncke, Jr., H.J. et al 'The Suture Repair of One-Millimeter Vessels, microvascular surgery' (1966) Report of First Conference; Oct. 6-7 pp. 24-35.
CCPR Centro de Cirurgia Plastica e Reabilitacao Up Lifting (Aptos Threads) http://ccpr.com.br/upl-l.htm, Aug. 19, 2002 pp. 1-2.
Dahlin, Lars, "Techniques of Peripheral Nerve Repair", Scandinavian Journal of Surgery 97: 310-316, 2008.
Datillo, Jr. P.P. et al 'Medical Textiles: Application of an Absorbable Barbed Bi-Directional Surgical Suture' (2002) The Journal of Textile and Apparel Technology and Management vol. 2, Issue 2, pp. 1-5.
Datillo, Jr., P. et al 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raúl et al., "Mechanics of Biomaterials: Sutures After the Surgery", Applications of Engineering Mechanics in Medicine, GED-University of Puerto Rico, Mayaguez May 2005, p. F1-F27.

Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Ingle, N.P. et al 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Khademhosseini, Ali et al., "Nanobiotechnology Drug Delivery and Tissue Engineering", Chemical Engineering Progress 102:38-42 (2006).
Kuniholm J.F. et al 'Automated Knot Tying for Fixation in Minimally Invasive, Robot Assisted Cardiac Surgery' Master of Science in Mechanical & Aerospace Engineering at North Carolina State University May 2003, 71 pages.
Lendelin, A. et al 'Biodegradable, Elastic Shape-Memory Polymers for Potential Biomedical Applications' (2002) Science vol. 296 pp. 1673-1676.
Lendelin, A. et al 'Shape-Memory Polymers' Agnew Chem Int. Ed. (2002) vol. 41 pp. 2034-2057.
Leung, J. et al 'Barbed, Bi-directional Medical Sutures: Biomechanical Properties and Wound Closure Efficacy Study' 2002 Society for Biomaterials 28th Annual Meeting Transactions 1 page.
Leung, J. et al 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Li, Y.Y. et al 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas, et al., "Neurotrophic factors release from nerve conduits for peripheral axonal regeneration", European Cells and Materials vol. 16; Suppl. 1 (2008), p. 14.
Mullner, "Metal Foam Has a Good Memory", Dec. 18, 2007 Original story at <http://www.physorg.com/news117214996.html>.
Nie, Zhihong and Kumacheva, Eugenia, "Patterning surfaces with functional polymers", Nature Materials vol. 7(2008): 277-290.
Paul, Malcolm D. and Rui Avelar, "Quill™ SRS Techniques & Procedures A Novel Approach to Soft Tissue Approximation", Canada, Angiotech Pharmaceuticals, Inc., First Edition 82007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition 82008: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D., "Bidirectional Barbed Sutures for Wound Closure: Evoluation and Applications", Journal of the American College of Certified Wound Specialists (2009) 1, 51-57.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.

(56) References Cited

OTHER PUBLICATIONS

Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic, et al., "Surface Nanopatterning to Control Cell Growth", Advanced Materials 2008(15): 1-5.
Rofin-Baasel 'Laser Marking on Plastic Materials' (2001) RB50.0, Rofin-Baasel Inc. 2 pages.
Scherman, Peter et al., "Sutures as longitudinal guides for the repair of nerve defects-Influence of suture numbers and reconstruction of nerve bifurcations", Restorative Neurology and Neuroscience 23 79-85.
Schmid A. et al 'The outspreading anchor cord. A material for arthroscopic suturing of a fresh anterior cruciate ligament rupture' Surgical Clinic of the University of Gottingen.
Semenov, G.M. et al 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Clin Plastic Surg 36 (2009); pp. 281-306.
Sulamanidze, M.A. et al 'Clinical aspects of bloodless facelift using APTOS filaments' A.V. Vishnevsky Institute of Surgery, Bol=shaya Serpukhovskaya ul, 7, 113811, Moscow, Russia (2002) pp. 24-34.
Sulamanidze, M.A. et al 'Facial lifing with APTOS threads' International Journal of Cosmetic Surgery and Aesthetic Dermatology (2001) No. 4 pp. 1-8.
Sulamanidze, M.A. et al 'Facial lifing with "Aptos" threads' http://fonendo.com (Jul. 18, 2001) pp. 1-4.
Sulamanidze, M.A. et al 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al 'Morphological foundations of facelift using APTOS filaments' Bolshaya Serpukhovskaya ul 27, 113811 Moscow, Russia (2002) pp. 1926.
Sulamanidze, MD, M.A., et al., "Soft tissue lifting in the mid-face: old philosophy, new approach-internal stitching technique (APTOS Needle)", Plastic and Aesthetic Surgery Clinic TOTAL SHARM, Moscow, Russia, (2005):15-29.
Sulzle, Inc. B.G. et al Drilled End Surgical Needles Jul. 2002 Syracuse, New York.
Surgical Specialties Corporation, "Wound Closure Catalog"; Summer 2005, 5 pages.
Tan E.L. et al., "A wireless, passive strain sensor based on the harmonic response of magnetically soft materials", Smart Materials and Structures 17 (2008): pp. 1-6.
Up Lifting (Aptos Threads), http://www.ccpr.com.br/upl-l.htm Aug. 19, 2002 pp. 1-2.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Communication from EPO re: 10000486 dated Apr. 4, 2011.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 23, 2007, 2 pages.
European Search Report for EP07016222 dated Jan. 7, 2008.
European Search Report for EP10000629.5 dated Mar. 10, 2010, 4 pages.
European Search Report re: EP10000486 dated Apr. 23, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10186592.1 dated Jan. 19, 2011, 2 pages.
Extended European Search Report re: 07015905.8 dated Oct. 2, 2007.
Extended European Search Report re: 07016222.7 dated Jan. 30, 2008.
International Preliminary Examination Report re: PCT/US1998/10478 dated Dec. 11, 1999.
International Preliminary Report re: PCT/US2009/040545 dated Oct. 19, 2010.
International Search Report for PCT/US1998/10478 dated Sep. 23, 1998.
International Search Report for PCT/US2002/027525 dated Dec. 9, 2002, 3 pages.
International Search Report for PCT/2003/30666 dated Dec. 15, 2004.
International Search Report for PCT/US2003/25088 dated Dec. 29, 2003.
International Search Report for PCT/US2009/040545 dated Oct. 29, 2009.
Partial European Search Report re: EP05025816 dated Mar. 20, 2006.
Supplementary European Search Report re: EP98923664 dated Jun. 12, 2001.
Supplementary European Search Report re: EP03785177 dated May 19, 2009.
U.S. Appl. No. 08/859,887, filed May 21, 1997.
U.S. Appl. No. 09/896,455, filed Jun. 29, 2001.
U.S. Appl. No. 09/919,750, filed Jul. 31, 2001.
U.S. Appl. No. 09/943,733, filed Aug. 31, 2001.
U.S. Appl. No. 10/216,516, filed Aug. 9, 2002.
U.S. Appl. No. 10/065,280, filed Sep. 30, 2002.
U.S. Appl. No. 10/065,279, filed Sep. 30, 2002.
U.S. Appl. No. 10/065,278, filed Sep. 30, 2002.
U.S. Appl. No. 10/914,755, filed Aug. 9, 2004.
U.S. Appl. No. 10/941,347, filed Sep. 15, 2004.
U.S. Appl. No. 11/154,230, filed Jun. 16, 2005.
U.S. Appl. No. 11/154,863, filed Jun. 16, 2005.
U.S. Appl. No. 11/307,901, filed Feb. 27, 2006.
U.S. Appl. No. 11/307,900, filed Feb. 27, 2006.
U.S. Appl. No. 11/440,621, filed May 25, 2006.
U.S. Appl. No. 11/440,631, filed May 25, 2006.
U.S. Appl. No. 11/968,494, filed Jan. 2, 2008.
U.S. Appl. No. 11/968,496, filed Jan. 2, 2008.
U.S. Appl. No. 12/119,749, filed May 13, 2008.
U.S. Appl. No. 12/340,530, filed Dec. 19, 2008.
U.S. Appl. No. 12/495,497, filed Jun. 30, 2009.
U.S. Appl. No. 61/357,018, filed Jun. 21, 2010.
U.S. Appl. No. 12/849,960, filed Aug. 4, 2010.
U.S. Appl. No. 12/849,969, filed Aug. 4, 2010.
U.S. Appl. No. 12/849,977, filed Aug. 4, 2010.
U.S. Appl. No. 12/849,983, filed Aug. 4, 2010.
U.S. Appl. No. 12/849,991, filed Aug. 4, 2010.
U.S. Appl. No. 12/850,035, filed Aug. 4, 2010.
U.S. Appl. No. 12/850,063, filed Aug. 4, 2010.
U.S. Appl. No. 13/164,438, filed Jun. 20, 2011.
U.S. Appl. No. 13/335,220, filed Dec. 22, 2011.
Madhave et al 'A biodegradable and biocompatible gecko-inspired tissue adhesive' PNAS 105(7) pp. 2307-2312 (2008).
Middleton and Tipton 'Synthetic Biodegradable Polymers as Medical Devices' (1998) Medical Plastics and Biomaterials Magazine, 9 pages.
International Search Report for PCT/US2003/30664 dated May 25, 2004.
U.S. Appl. No. 61/290,750, filed Dec. 29, 2009.
U.S. Appl. No. 61/296,721, filed Jan. 20, 2010.
U.S. Appl. No. 10/065,256, filed Sep. 30, 2002.
U.S. Appl. No. 11/691,845, filed Mar. 27, 2007.

(56) References Cited

OTHER PUBLICATIONS

U.S. Appl. No. 11/747,085, filed May 10, 2007.
U.S. Appl. No. 12/101,885, filed Apr. 11, 2008.
U.S. Appl. No. 12/340,444, filed Dec. 19, 2008.
U.S. Appl. No. 12/392,939, filed Feb. 25, 2009.
U.S. Appl. No. 12/849,884, filed Aug. 4, 2010.
U.S. Appl. No. 12/849,895, filed Aug. 4, 2010.
U.S. Appl. No. 12/849,901, filed Aug. 4, 2010.
U.S. Appl. No. 12/849,946, filed Aug. 4, 2010.
U.S. Appl. No. 12/850,397, filed Aug. 4, 2010.
U.S. Appl. No. 12/850,408, filed Aug. 4, 2010.
U.S. Appl. No. 12/850,433, filed Aug. 4, 2010.
U.S. Appl. No. 12/850,447, filed Aug. 4, 2010.
U.S. Appl. No. 12/850,455, filed Aug. 4, 2010.
U.S. Appl. No. 12/850,467, filed Aug. 4, 2010.
U.S. Appl. No. 12/850,480, filed Aug. 4, 2010.
U.S. Appl. No. 12/850,498, filed Aug. 4, 2010.
U.S. Appl. No. 12/972,802, filed Dec. 20, 2010.
Gross, R.A. et al 'Biodegradable Polymers for the Environment' Science (2002) vol. 297, Issue 5582 pp. 803.
Jeong, H.E. et al 'A nontransferring dry adhesive with hierarchial polymer nanohairs' PNAS 106 (14) pp. 5639-5644 (2009).
Martin, D.P. et al 'Medical applications of poly-4-hydroxybutyrate: a strong flexible absorbable biomaterial' Biochemical Engineering Journal vol. 16 (2003) pp. 97-105.
European Search Report for EP09014651 dated Jan. 12, 2010.
European Search Report re: 10004453 dated Jun. 15, 2010.
European Search Report for EP10011872 dated Apr. 20, 2011.
European Search Report for EP10012437 dated Apr. 28, 2011.
European Search Report for EP10184766 dated Apr. 20, 2011.
International Preliminary Report re: PCT/US2007/002688 dated Aug. 14, 2008.
International Preliminary Report re: PCT/US2008/060127 dated Oct. 13, 2009.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/041685 dated Oct. 26, 2010.
International Preliminary Report re: PCT/US2009/044274 dated Nov. 17, 2010.
International Preliminary Report re: PCT/US2011/035431 dated Nov. 6, 2012.
International Preliminary Report re: PCT/US2011/059238 dated May 7, 2013.
International Search Report for PCT/US1994/09631 dated Dec. 9, 1994.
International Search Report for PCT/US2002/20449 dated May 20, 2003.
International Search Report for PCT/US2003/030424 dated Nov. 1, 2004.
International Search Report for PCT/US2003/030664 dated May 25, 2004.
International Search Report re: PCT/US2003/030674 dated Sep. 2, 2004.
International Search Report re: PCT/US2004/014962 dated Feb. 24, 2005.
International Search Report for PCT/US2005/017028 dated Mar. 26, 2008.
International Search Report for PCT/US2007/002688 dated Oct. 22, 2007.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/063081 dated Aug. 2, 2010.
International Search Report for PCT/US2009/041685 dated Dec. 22, 2009.
International Search Report for PCT/US2009/044274 dated Jan. 15, 2010.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report re: PCT/US2011/035431 dated Jan. 12, 2012.
International Search Report re: PCT/US2011/040014 dated Feb. 9, 2012.
International Search Report for PCT/US2011/059238 dated May 21, 2012.
International Search Report for PCT/US2011/060069 dated May 18, 2012.
International Search Report for PCT/US2012/030441 dated Sep. 27, 2012.
International Search Report for PCT/US2012/041001 dated Sep. 26, 2012.
Singapore Search Report for Singapore Patent Application No. 201103117-6 dated Mar. 8, 2013.
Supplementary European Search Report re: EP03752630 dated Nov. 17, 2005.
Supplementary European Search Report re: 03770556 dated Nov. 17, 2005.
Supplementary European Search Report re: 03754965 dated Nov. 18, 2005.
Supplementary European Search Report re: 05750101 dated Apr. 7, 2010.
Supplementary European Search Report re: 07017663 dated Nov. 7, 2007.
Written Opinion of the International Searching Authority re: PCT/US2010/056898 dated Jul. 29, 2011.
Written Opinion of the International Searching Authority re: PCT/US2012/041001 dated Aug. 27, 2012.
Blaker, J.J. et al 'Development and Characterisation of silver-doped bioactive glass-coated sutures for tissue engineering and wound healing applications' Biomaterials (2004) vol. 25, No. 7-8 pp. 1319-1329.

\* cited by examiner

Fig. 2a
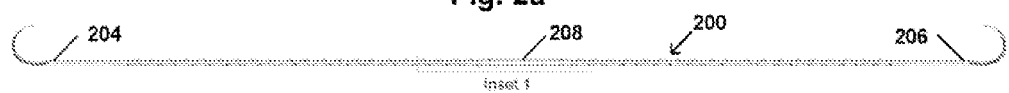
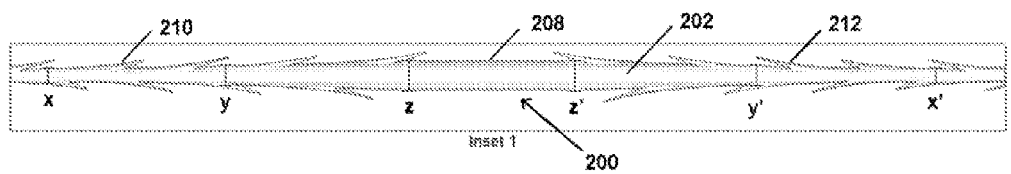
Fig. 2b

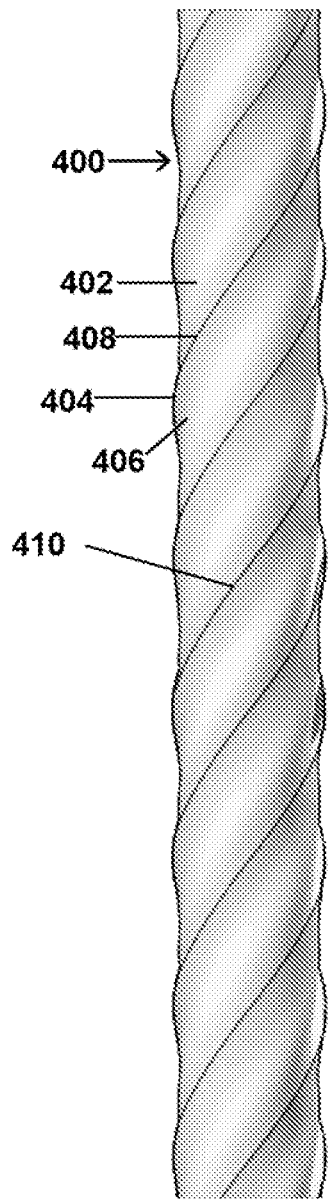 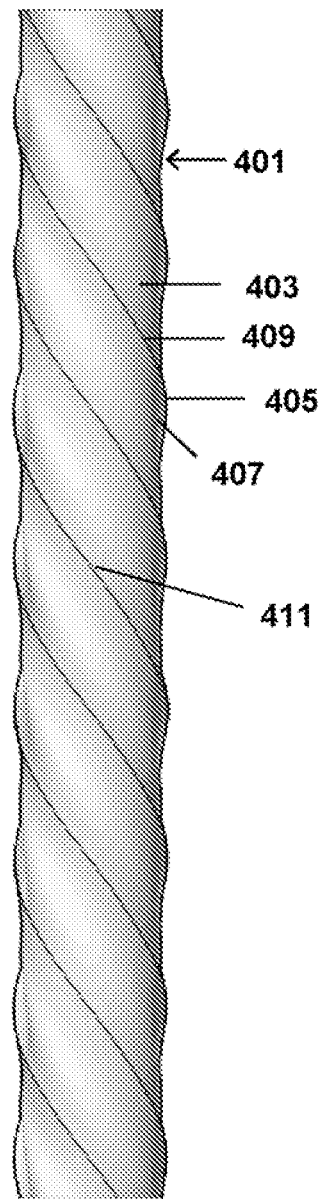

Fig. 7
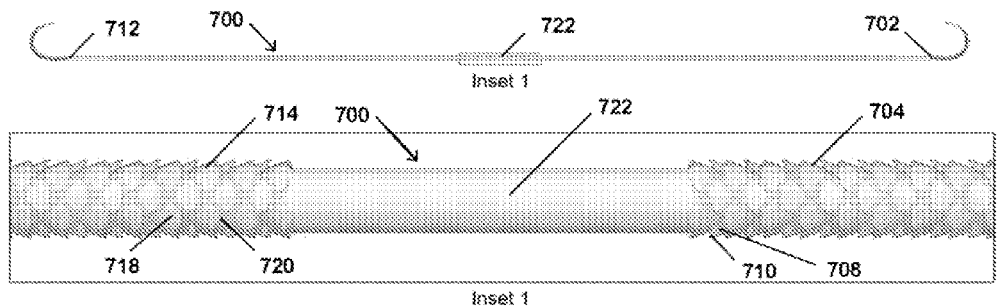
Fig. 8a
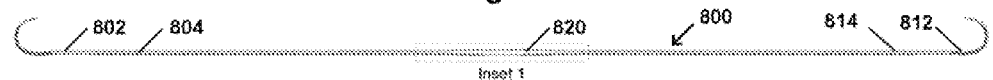
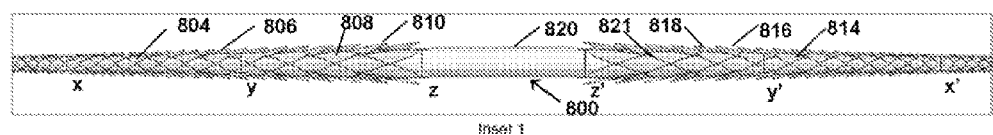
Fig. 8b
Fig. 9a
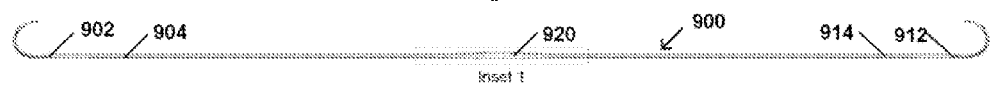
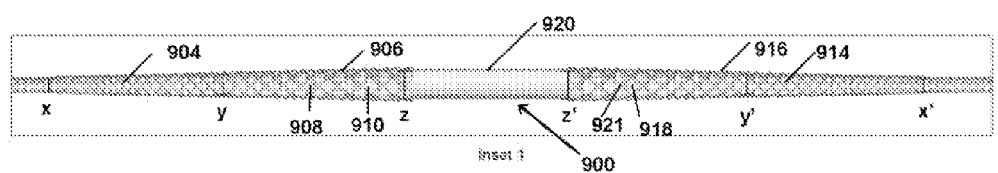
Fig. 9b

METHOD AND APPARATUS FOR FORMING RETAINERS ON A SUTURE

CLAIM TO PRIORITY

This application claims priority to U.S. Provisional Application No. 60/911,814, filed Apr. 13, 2007, which is incorporated herein by reference in its entirety.

FIELD OF THE INVENTION

The present invention relates generally to self-retaining systems for surgical procedures, methods of manufacturing self-retaining systems for surgical procedures, and their uses.

BACKGROUND

Wound closure devices such as sutures and staples have been widely used in superficial and deep surgical procedures in humans and animals for closing wounds, repairing traumatic injuries or defects, joining tissues together [bringing severed tissues into approximation, closing an anatomical space, affixing single or multiple tissue layers together, creating anastomoses between two hollow (luminal) structures, adjoining tissues, attaching or reattaching tissues to their proper anatomical location], attaching foreign elements to tissues (affixing medical implants, devices, prostheses and other functional or supportive devices), and for repositioning tissues to new anatomical locations (repairs, tissue elevations, tissue grafting and related procedures) to name but a few examples. Sutures typically consist of a filamentous suture thread attached to a needle with a sharp point (attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. U.S. 2004/0088003). Classically, the needle is advanced through the desired tissue on one side of the wound and then through the adjacent side of the wound to form a "loop" which is then completed by tying a knot in the suture.

Sutures materials are broadly classified as being bioabsorbable (i.e., they break down completely in the body over time), such as those composed of catgut, glycolic acid polymers and copolymers, lactic acid polymers and copolymers; or as being non-absorbable (permanent; nondegradable), such as those made of polyamide, polytetrafluoroethylene, polyether-ester, polyurethane, metal alloys, metal (e.g., stainless steel wire), polypropylene, polyethelene, silk, and cotton. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Nondegradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomoses. The present invention provides for polymeric formulations, surface properties, configurations and diameters designed to increase the holding power, durability and strength of self-retaining closure systems composed of both bioabsorbable and non-absorbable polymers.

A new type of suture has been designed with barbs, or with frusto-conical retainers, for engaging tissue when the suture is pulled in a direction other than that in which it was originally deployed in the tissue. Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. One of the earlier patents describing a barbed suture is U.S. Pat. No. 3,716,058, which discloses a suture having one or more relatively rigid barbs at its opposite ends; the presence of the barbs just at the ends of the suture would limit the barbs' effectiveness. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. Nos. 6,848,152, while methods of manufacturing sutures with frusto-conical retainers have also been described in European Patent 1 075 843.

Despite their advantages over conventional sutures, current designs of barbed sutures can break, slip through tissue, incompletely deploy, not fully anchor and/or rotate in situ, leading to suboptimal clinical results and limiting their utility. In the present invention, novel tissue retainer configurations, secondary retainer structures and expanded segment suture configurations are described that increase the ability of the self-retaining sutures to anchor into their surrounding tissue, strengthen their hold, increase the amount of tension they can withstand (without breakage or slippage) and increase their clinical performance.

SUMMARY

Sutures may be configured to more effectively distribute or resist tensions upon them when deployed in tissue.

In one aspect, a suture may include an expanded section disposed away from either end of the suture.

In another aspect, a suture may include one or more tissue retainers having an uneven or roughened surface.

In another aspect, a suture may include a continuous helical tissue retainer that is unidirectional.

In another aspect, a suture may include a continuous helical tissue retainer that is bidirectional. In the bidirectional configuration, the helix is oriented in one direction projecting "away" from the needle until the midpoint (or transition point) of the suture is reached; at this point the configuration of the helix reverses itself 180° along the remaining length of the suture thread before attaching to a second needle at the opposite end.

In another aspect, a method of manufacturing a helical self-retaining suture may include cutting a continuous helical tissue retainer in one chiral direction angled away from the suture deployment end, and a second continuous helical tissue retainer cut in the opposite chiral direction also angled away from the deployment end.

In another aspect, a method of manufacturing a bidirectional helical self-retaining suture may include cutting a continuous helical tissue retainer in one chiral direction angled away from a first suture deployment end and a second continuous helical tissue retainer cut in the opposite chiral direction also angled away from the first suture deployment end, both at a first portion of the suture that is proximal to the first suture deployment end. The method may further include cutting a continuous helical tissue retainer in one chiral direction angled away from a second suture deployment end and a second continuous helical tissue retainer cut in the opposite chiral direction also angled away from the second suture deployment end, both at a second portion of the suture that is proximal to the second suture deployment end and that is disposed away from the first portion In yet another aspect, a suture may include tissue retainer "scales" that increase the percentage of the surface area covered by retaining elements as compared to intermittent "barb" configurations. Such tissue retainer scales may include pointed or rounded tissue penetrating edges.

In another aspect, a method of manufacturing a "scaled" self-retaining suture may include cutting a continuous helical tissue retainer in one chiral direction angled away from the suture deployment end, while a second continuous helical tissue retainer is cut in the opposite chiral direction and (also angled away from the suture deployment end).

In yet another aspect, a suture may include one or more primary tissue retainers, with at least one such primary tissue retainer that further includes one or more secondary tissue retainers. Such secondary tissue retainers may include flanges, barbs, and filaments.

In yet another aspect, the surface of the portion of the suture material that is not composed of primary tissue retainers (i.e., the "unbarbed" areas of the thread), are modified such that they further include one or more secondary tissue retainers. Such secondary tissue retainers may include flanges, barbs, and filaments.

In yet another aspect, the surface of the portion of the suture material that is not composed of primary tissue retainers (i.e., the "non-barbed" areas of the thread) and the primary tissue retainers themselves are both modified to further include one or more secondary tissue retainers. Such secondary tissue retainers may include flanges, barbs, and filaments.

In a further aspect, a method of making a self-retaining suture includes the step of cutting intersecting helical escarpments into the circumferential periphery of a suture body. Such helical escarpments may intersect due to differing pitches or opposing chirality of the helices.

In another aspect, a method of making a self retaining suture includes an expanded section of the thread such that the diameter of the expanded portion of the thread is greater than the diameter the end of the suture, or, if the suture is adapted for deployment with a needle, than the diameter of the needle.

In yet another aspect, a method of making a bidirectional self retaining suture includes an expanded section of the thread such that the diameter of the thread at a specified distance from either needle attachment site (this distance will vary depending upon the clinical indication) is greater than the diameter of the needles that are attached to it; from the point where the barbed suture thread diameter is greatest, the diameter of the thread then tapers down (the rate and length of the tapering segment will vary depending upon the clinical indication) as it approaches the needle attachment sites until the thread diameter is equal to, or smaller than, the diameter of the needles it is attached to.

The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIGS. 2a and 2b are perspective views of an embodiment according to the present invention of a self-retaining suture having an expanded transition segment.

FIGS. 4a and 4b are perspective views of embodiments according to the present invention of single helix self-retaining sutures.

FIG. 7 is a perspective view of a further embodiment according to the present invention of a bidirectional scaled self-retaining suture having rounded retainers in an expanded position.

FIGS. 8a and 8b are perspective views of an embodiment according to the present invention of a bidirectional double helix self-retaining suture having an expanded transition segment.

FIGS. 9a and 9b are perspective views of a further embodiment according to the present invention of a bidirectional scaled self-retaining suture having rounded retainers and an expanded transition segment.

DETAILED DESCRIPTION OF THE INVENTION

Figure 1A:
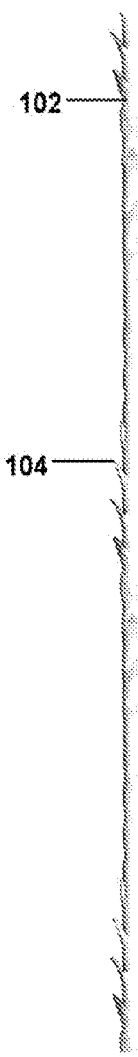
FIGS. 1a, 1b, and 1c are perspective views of an embodiment according to the present invention of a self-retaining suture having uneven-surfaced retainers.
Figure 1B:
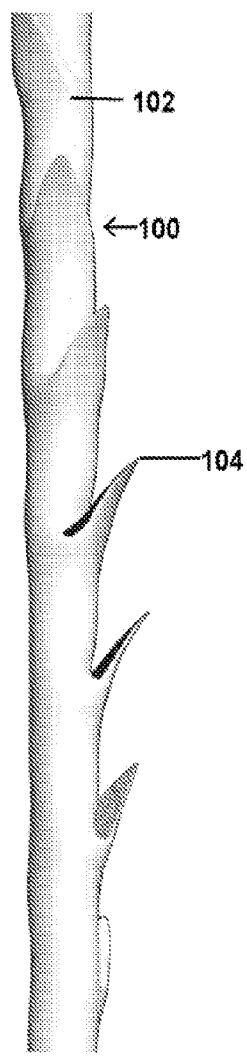
Figure 1C:
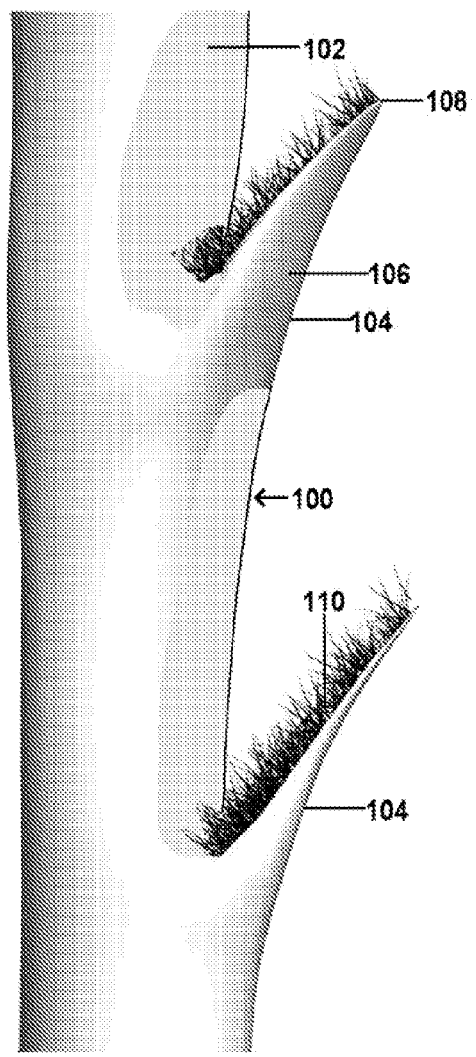

Prior to setting forth the invention, it may be helpful to an understanding thereof to first set forth definitions of certain terms that are used hereinafter.

"Self-retaining system" refers to a self-retaining suture together with means for deploying the suture into tissue. Such deployment means include, without limitation, suture needles and other deployment devices as well as sufficiently rigid and sharp ends on the suture itself to penetrate tissue.

"Self-retaining suture" refers to a suture that does not require a knot or a suture anchor at its end in order to maintain its position into which it is deployed during a surgical procedure. These may be monofilament sutures or braided sutures, and are positioned in tissue in two stages, namely deployment and affixation, and include at least one tissue retainer.

"Tissue retainer" (or simply "retainer") or "barb" refers to a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction (i.e. they lie flat when pulled in the deployment direction; and open or "fan out" when pulled in a direction contrary to the deployment direction). As the tissue-penetrating end of each retainer faces or points away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from their deployment positions (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self retaining suture in place.

"Retainer configurations" refers to configurations of tissue retainers and can include features such as size, shape, surface characteristics, and so forth. These are sometimes also referred to as "barb configurations".

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transitional segment located between the two barb orientations.

"Transition segment" refers to a retainer-free (barb-free) portion of a bidirectional suture located between a first set of retainers (barbs) oriented in one direction and a second set of retainers (barbs) oriented in another direction.

"Suture thread" refers to the filamentary body component of the suture, and, for sutures requiring needle deployment, does not include the suture needle. The suture thread may be monofilamentary, or, multifilamentary.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable (also referred to as "biodegradable" or "bioabsorbable") suture" refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination or these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used in the present invention can be linear polymers, branched polymers or multi-axial polymers. Examples of multi-axial polymers used in sutures are described in U.S. Patent Application Publication Nos. 20020161168, 20040024169, and 20040116620. Sutures made from degradable suture material lose tensile strength as the material degrades.

"Non-degradable (also referred to as "non-absorbable") suture" refers to a suture comprising material that is not degraded by chain scission such as chemical reaction processes (e.g., hydrolysis, oxidation/reduction, enzymatic mechanisms or a combination or these) or by a thermal or photolytic process. Non-degradable suture material includes polyamide (also known as nylon, such as nylon 6 and nylon 6.6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Suture deployment end" refers to an end of the suture to be deployed into tissue; one or both ends of the suture may be suture deployment ends. The suture deployment end may be attached to deployment means such as a suture needle, or may be sufficiently sharp and rigid to penetrate tissue on its own.

"Armed suture" refers to a suture having a suture needle on at least one suture deployment end.

"Needle attachment" refers to the attachment of a needle to a suture requiring same for deployment into tissue, and can include methods such as crimping, swaging, using adhesives, and so forth. The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging whereby the suture material is inserted into a channel at the blunt end of the needle which is then deformed to a final shape to hold the suture and needle together. As such, atraumatic needles do not require extra time on site for threading and the suture end at the needle attachment site is smaller than the needle body. In the traumatic needle the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles would be ideal.

Suture needles may also be classified according to their point geometry. For example, needles may be (i) "tapered" whereby the needle body is round and tapers smoothly to a point; (ii) "cutting" whereby the needle body is triangular and has sharpened cutting edge on the inside; (iii) "reverse cutting" whereby the cutting edge is on the outside; (iv) "trocar point" or "tapercut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030 (Mani, Inc., Japan); and 5,464,422 (W. L. Gore, Newark, Del.); and 5,941,899; 5,425,746; 5,306,288 and 5,156,615 (US Surgical Corp., Norwalk, Conn.); and 5,312,422 (Linvatec Corp., Largo, Fla.); and 7,063,716 (Tyco Healthcare, North Haven, Conn.). Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a gunshot, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

"Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects achieve a downward pull on this tissue and the underlying ligaments, and fat descends into the plane between the superficial and deep facial fascia, thus allowing facial tissue to sag. Face-lift procedures are designed to lift these sagging tissues, and are one example of a more general class of medical procedure known as a tissue elevation procedure. More generally, a tissue elevation procedure reverses the appearance change that results from gravitation effects over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing/replacing damaged or diseased organs and tissues. While normally composed of biologically compatible synthetic materials (e.g., medical-grade stainless steel, titanium and other metals: polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopaedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

As discussed above, the present invention provides compositions, configurations, methods of manufacturing and methods of using self-retaining systems in surgical procedures which greatly increase their ability to anchor into the surrounding tissue to provide superior holding strength and improve clinical performance.

A. Self-Retaining Sutures

Self-retaining sutures (including barbed sutures) differ from conventional sutures in that they possess numerous tiny tissue retainers (such as barbs) which anchor into the tissue following deployment and resist movement of the suture in a direction opposite to that in which the retainers face, thereby eliminating the need to tie knots to affix adjacent tissues together (a "knotless" closure). By eliminating knot tying, associated complications are eliminated, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (they create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time). Thus, knotless sutures not only allow patients to experience an improved clinical outcome, but they also save time and costs associated with extended surgeries and follow-up treatments.

Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures effected with plain sutures or staples.

The ability of self-retaining sutures to anchor and hold tissues in place even in the absence of tension applied to the suture is a feature that also provides superiority over plain sutures. When closing a wound that is under tension, this advantage manifests itself in several ways: (i) a multiplicity of retainers can dissipate tension along the entire length of the suture (providing hundreds of "anchor" points as opposed to knotted interrupted sutures which concentrate the tension at discrete points; this produces a superior cosmetic result and lessens the chance that the suture will "slip" or pull through); (ii) complicated wound geometries can be closed (circles, arcs, jagged edges) in a uniform manner with more precision and accuracy than can be achieved with interrupted sutures; (iii) they eliminate the need for a "third hand" which is often required for maintaining tension across the wound during traditional suturing and knot tying (to prevent "slippage" when tension is momentarily released during tying); (iv) they are superior in procedures where knot tying is technically difficult, such as in deep wounds or laparoscopic procedures; and (v) they can be used to approximate and hold the wound prior to definitive closure. As a result, self retaining sutures provide easier handling in anatomically tight or deep places (such as the pelvis, abdomen and thorax) and make it easier to approximate tissues in laparoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

Self retaining sutures also lend themselves to a variety of specialized indications; for example, they are suitable for tissue elevation procedures where tissue is moved from its previous location and repositioned into a new anatomical location (this is typically performed in cosmetic procedures where "drooping" tissue is elevated and fixed in a more "youthful" position; or where "out-of-position" tissue is moved back to its correct anatomical location). Such procedures include facelifts, brow lifts, breast lifts, buttocks lifts, and so forth.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over the remainder of the thread (as described with barbed retainers in U.S. Pat. Nos. 5,931,855 and. 6,241,747).

Although any number of sequential or intermittent configurations of retainers are possible, a common form involves a needle at one end, followed by barbs projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also face away from the nearest needle). Put another way, the barbs on both "halves" of a bidirectional self-retaining suture point towards the middle, with a transition segment (lacking retainers) interspersed between them, and with a needle attached to either end.

Despite the multitude of advantages of unidirectional and bidirectional self retaining sutures, there remains a need to improve upon the design of the suture such that a variety of common limitations can be eliminated. Specifically, several problems common to existing self retaining sutures can be addressed by the embodiments of this invention, including, but not limited to: (i) retainers or barbs that are fragile and break (or bend back) when deployed in tissue; (ii) inadequate "hold" provided by the retainers for some surgical procedures; resulting in retainers or barbs do not sufficiently anchor in the surrounding tissue and "pull through;" (iii) insufficient contact between the retainers and the surrounding tissue (often occurring when the thread diameter is too small relative to the diameter of the hole created by a larger needle; this limits the ability of the retainers to contact and "grip" the surrounding tissue); (iv) breakage of the self retaining suture during tensioning and wound apposition; and (v) rotation and slippage of the retainers after deployment. The following self retaining sutures solve many of the aforementioned problems.

B. Tissue Engagement Surface Configurations

The affixation of self-retaining sutures after deployment entails the penetration of retainer ends into the surrounding tissue resulting in tissue being caught between the retainer and the suture body. The inner surface of the retainer that is actually in contact with the tissue that is caught between the retainer and the suture body, herein referred to as the "tissue engagement surface" or "inner retainer surface," can be adapted to better engage the tissue. With reference to FIG. 1, suture 100 includes retainer 104 projecting from suture body 102, where retainer 104 includes retainer body 106, tissue-penetrating end 108, and tissue engagement surface 110. As shown in FIG. 1, the tissue engagement surface 110 of retainer 104 can be provided with an uneven configuration thereby increasing the surface area in contact with tissue and enhancing the resistance of the suture 100 to movement in a direction other than the deployment direction. It is to be understood that the term "uneven" as used herein indicates any surface configuration that is not flat and therefore comprises a greater surface area than would a comparably-sized flat surface. As such, the term may encompass, without limitation, surfaces that are rippled, corrugated, rough, dimpled, serrated, knobby, ridged, filamented, concave, convex, and so forth. The increased surface area not only increases the interaction between the suture material and the tissue, it also provides a supportive matrix for cellular attachment and ingrowth that can facilitate healing. This can be expected not only to increase the holding power of the self retaining suture acutely (i.e. shortly after deployment) due to the increased area of contact between the suture and the tissue, but as healing progresses, the holding strength will be further increased due to the attachment and growth of healing tissue onto the tissue engagement surface.

The tissue engagement surface can be provided with an uneven configuration either during or after the manufacture of the self-retaining suture. In the former case, a method of forming retainers on a suture can include: providing a suture having a longitudinal axis and a circumferential periphery, a cutter, a displacer for pivoting the cutter, the suture, or both about the longitudinal axis; engaging the cutter with the suture; and, cutting an uneven-surfaced escarpment into the periphery of the suture. To achieve a rough surface, the cutter may be a grinding wheel, a burr grinder, have an abrasive surface, etc., while other uneven surface configurations may be achieved with cutters such as, without limitation, arcuate or corrugated blades.

Figure 1D:
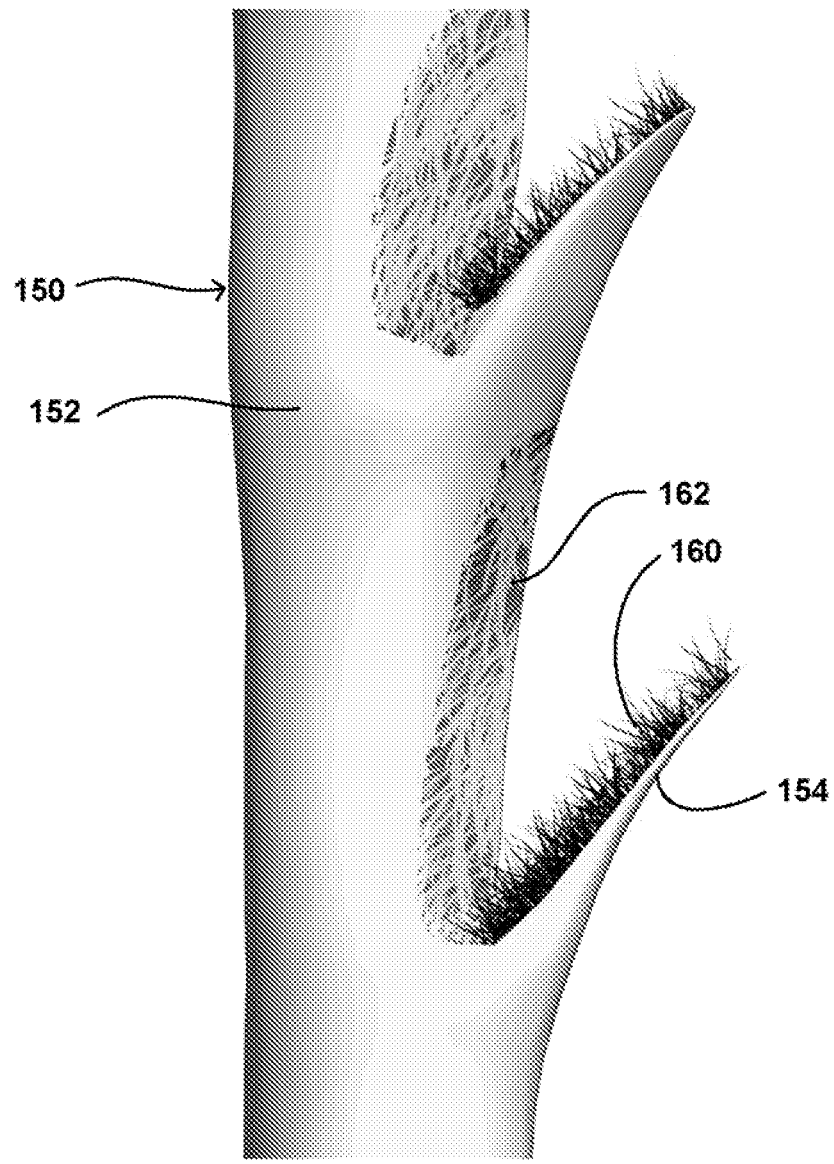
FIG. 1d is a perspective view of a further embodiment according to the present invention of a self-retaining suture having uneven-surfaced retainers.

As shown in FIG. 1d, providing the surface 162 of the body 152 of suture 150 that faces the inner surface 160 of retainer 154 with an uneven configuration can further enhance surface area, increase the interaction between the suture material and the tissue, increase tissue retention and increase resistance to movement in a direction other than the deployment direction. As with self-retaining sutures having an uneven inner retainer surface, uneven tissue engagement surfaces on both retainer and suture body in sutures such as the one in FIG. 1d may similarly be formed during or after the manufacture of the self-retaining suture. To achieve rough surfaces on both aspects of the suture, the cutter may be a grinding wheel (roughened on both sides), a burr grinder, have an double-sided abrasive surface, etc., while other uneven surface configurations may be achieved with cutters such as, without limitation, arcuate or corrugated blades. Further, cutters creating uneven tissue engagement surfaces on both suture body and retainer may be employed during suture manufacture and, if desired, selected tissue engagement surfaces having the resultant uneven configurations may subsequently be scraped or polished to provide a smoother surface. This embodiment can be expected to further increase the immediate holding power of the self retaining suture acutely due to the increased area of contact between the suture and the tissue and provide greater holding strength as healing tissue attaches and grows onto both surfaces.

Alternatively, an uneven tissue engagement surface and/or suture body surface configuration can be obtained after the manufacture of the self-retaining suture. A method of forming retainers on a suture can include: providing a suture having a longitudinal axis and a circumferential periphery, a cutter, and a displacer for pivoting the cutter, the suture, or both about the longitudinal axis; engaging the cutter with the suture; cutting an escarpment into the periphery of the suture; and rendering uneven at least a portion of at least one (or both) cut surface(s) of the escarpment. The last step may include, without limitation, treating that portion with an abrasive agent, a polymerising agent, an acid etchant, or a base etchant.

C. Diameter Expansion

Both unidirectional and bidirectional self retaining sutures can be provided with an expanded thread section between the two ends. For example, a suture may include an expanded section of the thread such that the diameter of the expanded portion of the thread is greater than the diameter of the end of the suture, or, if the suture is adapted for deployment with a needle that has a greater diameter than the end of the suture, than the diameter of the needle. For sutures adapted for deployment with one or more needles, the diameter of the thread at a specified distance from the needle attachment site (this distance will vary depending upon the clinical indication) is greater than the diameter of the needle that is attached to it. From the point where the barbed suture thread diameter is greatest, the diameter of the thread then tapers down as it approaches the needle attachment site until the thread diameter is equal to, or smaller than, the diameter of the needle to be used to deploy the suture (at the needle's widest point). The rate, distance, degree and length of the tapering of the thread can be adjusted depending upon the clinical indication.

In another aspect, a bidirectional barbed suture may include an expanded segment of the thread which is located at the transition point where the barb configurations change orientation (typically, but not always, located at or near the middle of the thread). The maximum diameter of the suture thread occurs somewhere along the transition segment and is greater than the diameter of either end of the suture, or, in the case of armed sutures, the deployment needle attached to the suture end. In this aspect, the diameter of the thread is greatest at the transition point (typically in the middle) and then tapers down from this segment in both directions towards the needle attachment point until the thread diameter is equal to, or smaller than, the diameter of the ends of the suture or, in the case of armed sutures, the diameter of the needle (at the needle's widest point) attached to it. The rate, distance, degree and length of the tapering of the thread can be adjusted depending upon the clinical indication. In the case of bidirectional self-retaining sutures, one end of the suture is deployed into the tissue at a substantially central first point of the suture path and then the other end is deployed from a second point near the first point but in the opposite direction, in order to avoid engaging the retainers in tissue prior to completing the full deployment of the suture along the desired path. Thus, in the case of bidirectional sutures, a transitional segment of the suture, that segment between a first retainer or plurality of retainers facing away from a first end of the suture and a second retainer or plurality of retainers facing away from a second end of the suture, may be the portion of the suture upon which the greatest tension is exerted and therefore most likely to fail (break and/or pull through), both during deployment and/or after affixation, as the suture is effectively pulled from substantially opposing directions during both deployment and affixation. The portion of the suture upon which the magnitude of the longitudinal forces is greatest can be enhanced to resist those forces by increasing the diameter of the suture thread at that portion; thus reducing the likelihood that it will break. In addition, the larger diameter suture thread will be forced into a smaller diameter "hole" created by the needle (or the smaller diameter suture end); this has the effect of "sinking" the expanded suture thread into the needle track, increasing the likelihood that the retainers will contact and embed in the surrounding tissue, and reducing the probability that the self retaining suture will pull through the tissue when tension is applied to it (something that is more prevalent when the needle track is larger than the thread diameter, as is the case with previously described barbed sutures). This embodiment is not only useful for wound closure applications, but is particularly helpful for tissue retention applications, an example of which is described below in relation to FIG. 3e.

The expanded thread segment can be created during manufacture of the suture thread (by, for example, extruding a larger amount of suture material for a particular length of a suture thread during an extrusion manufacturing process, cutting or stamping a suture thread with an expanded diameter portion, and so forth), or after the manufacture of the suture thread (by, for example, cutting material away from the ends of a suture thread, adding material to the desired portion of the thread, and so forth).

Referring now to FIGS. 2a and 2b, bidirectional suture 200 includes first plurality of retainers 210 facing substantially toward and pointing substantially away from first suture end 204 and second plurality of retainers 212 facing substantially toward and pointing substantially away from second suture end 206 (which may or may not correspond to the actual mid-point of the suture, depending on the arrangement of retainers). As shown in FIG. 2a, to enhance the ability of transition segment 208 to withstand tension and increase tissue hold during clinical deployment, transition segment 208 can be expanded such that the diameter at transition segment 208 of suture 200 is greater than the diameter of suture 200 at either end 204 or 206. Further, as shown in FIG. 2b, such expansion can be incremental, with the diameter increasing from each end 204 and 206 of suture 200 and reaching a maximum at transition segment 208; the incremental expansion may commence at a point outside the transitional segment, such that some part of the retainer-bearing portions of the suture thread may also have a greater diameter than that of a suture end. The actual proportion of the diameter increase will depend on several factors, including without limitation the initial diameter at the ends of the suture, the nature of the tissue being sutured, the strength and flexibility of the suture material, the degree of tissue "anchorage" required, the amount of tension across the wound, etc. In FIG. 2b, for instance, the ratio of the suture diameter at ends 204 and 206 to increasingly central suture diameter at positions x and x', y and y', and z and z', where z and z' define the boundaries of transition segment 208, rise respectively from 1:1, 1:1.5, and 1:2. The precise values and ratios suitable for any particular self-retaining suture having an expanded diameter at least some portion of the transition segment will vary depending on the purpose of the suture, the tissues for which it is intended, the suture material, and so forth. It should also be noted that for many indications the transition segment may be quite short; it is exaggerated in these figures for illustrative purposes.

Figure 3A:
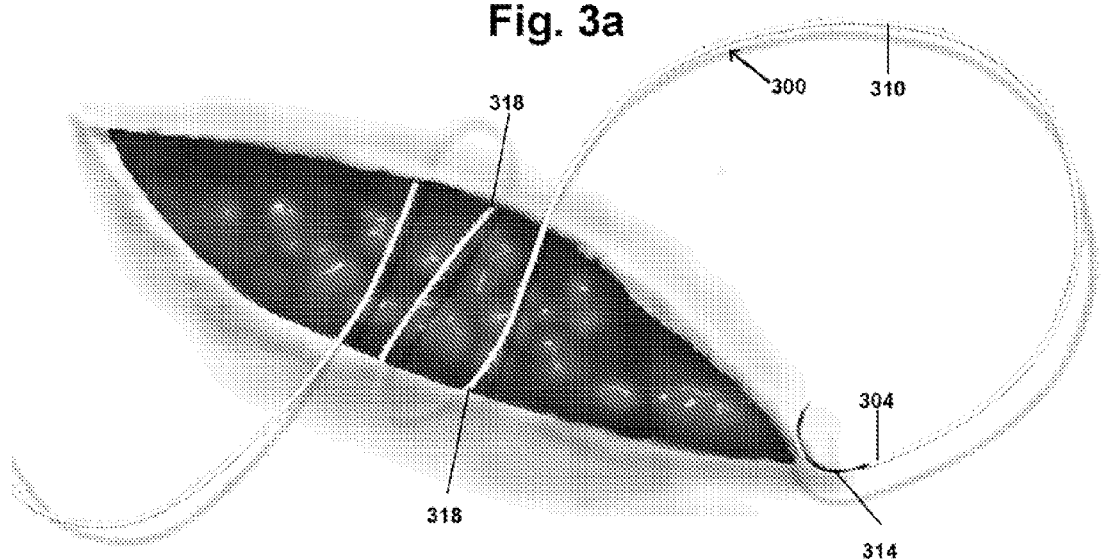
FIGS. 3a, 3b, 3c, and 3d are perspective views of a use of an embodiment according to the present invention of a self-retaining suture having an expanded transition segment.
Figure 3B:
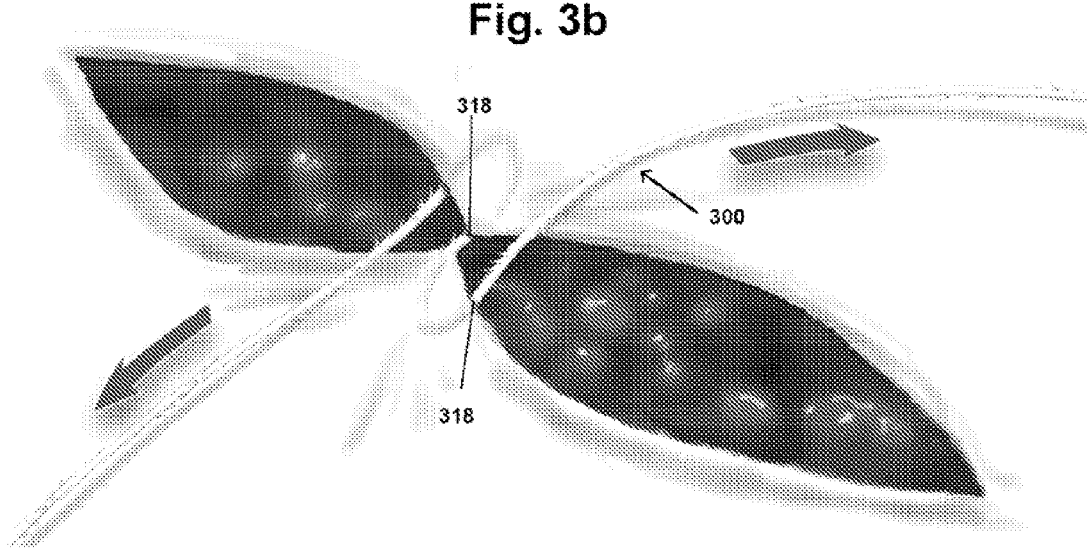
Figure 3C:
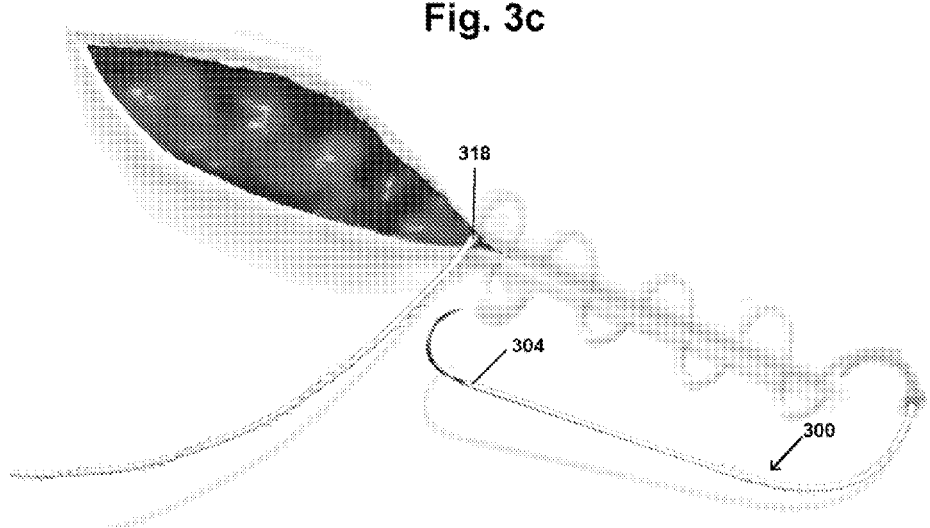
Figure 3D:
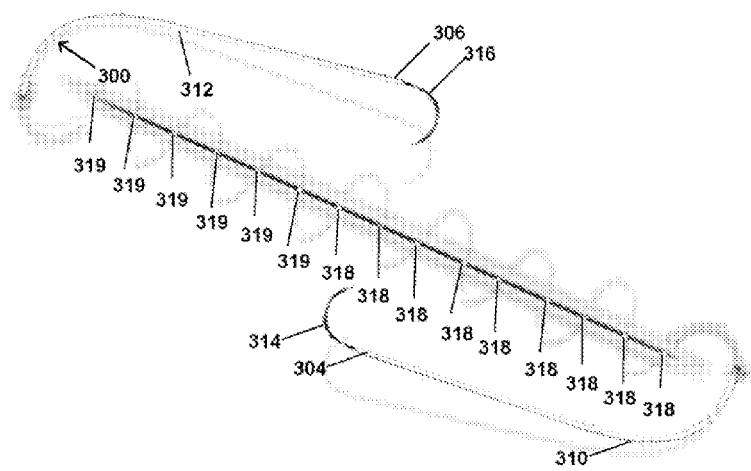
Figure 3E:
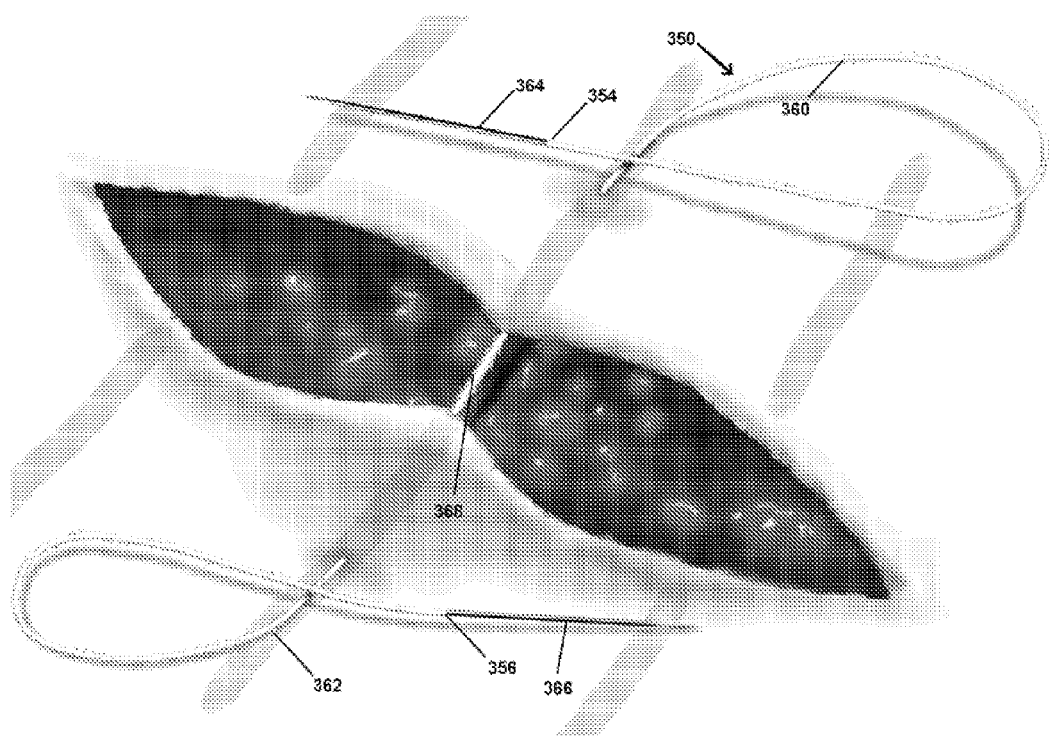
FIG. 3e is a perspective view of a use of an embodiment according to the present invention of a self-retaining suture having an expanded transition segment.

A use of a bidirectional self-retaining suture 300 having an expanded transition segment 368 is depicted in FIG. 3e. With reference to FIG. 3a, suture 300 attached to needle 314 at suture end 304 is deployed in a subcuticular stitch through wound edges at about the central portion of the wound. First plurality of retainers 310, disposed proximal to and facing suture end 304, are pulled through tissue at the wound edges in the deployment direction. As illustrated in FIG. 3b, upon subcuticularly connecting wound edges with two stitches 318 running from the center to the end of the wound, suture 300 is pulled in the deployment direction to approximate the wound edges together. With each pair of subcuticular stitches 318, suture 300 is pulled in the deployment direction to progressively approximate wound edges until the last stitch in that deployment direction is at an end of the wound and the portion of the wound stitched together is closed, as shown in FIG. 3c, with the retainer-free segment (the part of the thread where one barb orientation transitions into the opposite barb orientation) remaining at the central portion of the wound. Then, as illustrated in FIG. 3d, the process is repeated for the rest of the wound with a second set of subcuticular stitches 319 deployed with needle 316 at suture end 306 and second plurality of retainers 312, resulting in a closed wound. When, on the second half of the wound closure surgery, suture 300 is drawn through the tissue to approximate the wound edges on the open remainder of the wound, the act of pulling the suture 300 in the second deployment direction (that is, towards the second end of the wound) comprises the necessary affixation force for the first plurality of retainers 310, thus causing first plurality of retainers 310 to engage the tissue. Conversely, once suture 300 is pulled sufficiently tightly to close the second half of the wound, the engagement force of the tissue exerted against the first plurality of retainers 310 affixes the second plurality of retainers 312. The expansion of some or part of the transition segment (208 in FIG. 2b, 368 in FIG. 3e) renders the suture 300 more resistant to failure (breakage) caused by the resultant opposing longitudinal tissue engagement forces and the expanded segment also anchors better into the subcuticular tissue, lessening the chances that the retainers will "pull through" or disengage if the wound is under tension. Moreover, as the transition segment is the last portion of the suture 300 to be deployed into the tissue and as the diameter of the tissue perforation made by the needle (or sharpened end of the suture or other deployment element, whatever the case may be) is smaller than the diameter of the expansion portion of the suture, the engagement of the expansion portion of the suture in the tissue entails the exertion of an outwardly radial force from the expansion portion of the suture on the surrounding tissue. As the tissue is elastic and so in return exerts a force back upon the expansion portion of the suture, the positioning of the expansion portion of the suture in the tissue is better secured and thus the suture 300 can better resist movement in the tissue due to the longitudinal forces acting on the deployed suture.

Expanded diameter self-retaining sutures are also useful for tissue approximation procedures, that is, those used to bring wounds under high tension closer together to hold them in place while a definitive surface closure is performed; this is illustrated by way of example in FIG. 3e. In a gaping wound (or a wound that would be difficult to bring together because of tension across it), a bidirectional self-retaining suture 350 is deployed to bring the tissues into closer approximation. In this procedure, needle 364 at suture end 354 (and proximal to first plurality of retainers 360, which are oriented or pointing away from needle 364) is inserted through the wound edge, passed radially outwards from wound, and withdrawn at a distance from the wound edge; the distance is selected to suit the nature of the wound and surrounding tissues, while bearing in mind that the farther the distance, the greater the holding strength). The procedure is then repeated on the other side of the wound with the opposite needle 366 at suture end 356 and the second plurality of retainers 362 oriented or pointing in the opposite direction opposite to the first plurality of retainers 360. For large wounds, several self-retaining sutures may be required. The tissue can then be progressively "ratcheted" together over the retainers until it is as close together as is required (or as is prudent). Having an expanded diameter at the transition segment 368 that tapers down towards a needle (on either end of suture 350) not only provides additional strength where it is needed most (at the center), but also increases the anchorage of the retainers 360 and 362 into the tissue on either side of the wound; thereby increasing the amount of tension the suture can withstand without pulling through the tissue.

While these examples illustrate the deployment of a self-retaining suture in skin closure and in tissue approximation procedures, it is to be understood that the benefits of using a suture with an expanded diameter along part or all of its transition segment (or, in the case of sutures that are not bidirectional, at some portion away from an end of the suture) can be enjoyed in other suture applications, such as other types of wound closure, tissue repositioning, and so forth. It should also be obvious to one of skill in the art that an expanded diameter segment would be of utility in the creation of any self retaining suture including retainer designs described in the prior art as well as in all the novel retainer designs disclosed in the present invention (in Sections B, D and E).

D. Helical Retainer Configurations

Uneven tension distribution on retainers may also cause suture failure, particularly where retainers are spaced too far apart from one another, the retainer configuration allows "twisting" after deployment, or where there are not enough retainers (or anchorage points) present to provide sufficient holding strength. A self-retaining suture can include improved retainer configurations, such as helical retainers (along the continuous length of which tension is distributed substantially evenly) and scaled retainers (which provide maximal tissue engagement surface area, thereby optimising the tension distribution). For example, with reference to FIG. 4a, a self-retaining suture 400 can include a helical retainer 404 disposed along at least part of the suture body 402, the helical retainer 404 including a retainer body 408 and a tissue penetrating edge 410, the retainer 404 facing in a direction and being adapted for resisting movement of the suture, when in tissue, in an opposite direction from the direction in which it faces. Such helical self-retaining suture may be unidirectional or bidirectional, wherein the latter can have the helical retainer disposed at least in part proximal to and with the penetrating edge 410 facing away from one end of the suture and can include a second helical retainer disposed at least in part proximal to and with the penetrating edge 410 facing away from the other end of the suture, the suture including a retainer-free mid-section.

FIG. 4b also discloses a helical self-retaining suture in the deployment position (that is, the unexpanded position), the suture 401 including a helical retainer 405 disposed along at least part of the suture body 403, the helical retainer 405 including a retainer body 409 and a tissue penetrating edge 411. The retainer 405 also faces in a direction and is adapted for resisting movement of the suture, when in tissue, in an opposite direction from the direction in which it faces. However, helical retainer 404 of suture 400 is chirally opposite to helical retainer 405 of suture 401.

The helical self-retaining sutures of FIGS. 4a and 4b can be produced by a method including (i) providing a suture having a longitudinal axis and a circumference; a cutter; and, a displacer for longitudinally displacing and pivoting about the longitudinal axis at least one of the cutter and suture relative to one another; (ii) placing the cutter and suture into cutting engagement at a transverse cut angle; and, (iii) cutting a first helical circumferential escarpment about the suture.

The pivoting displacement of the cutter and/or suture relative to each other can be effected in one of several ways. For example, one of the cutter or suture may be moved: the cutter may revolve in a path about the circumference of the suture or the suture may be rotated on its longitudinal axis. Alternatively, both suture and cutter may be pivotally displaced about the longitudinal axis of the suture, the suture being rotated while the cutter revolves. In the latter case, suture and cutter may be pivoted either in the same direction or in opposing directions about the longitudinal axis. If both cutter and suture are pivoted in the same direction, the angular velocity at which each is pivoted about the longitudinal axis must differ in order to effect a circumferential escarpment on the suture. Where only one of the two is moved, or both are moved in opposing directions, the pivot velocity does not affect the cutting of the circumferential escarpment, although there may be operational limitations on the pivot velocity.

Similarly, the longitudinal displacement of the suture and cutter relative to one another may be achieved in several ways. If it is desired to only move one of the two, then either the suture can be moved while the cutter remains longitudinally stationary (for example, without limitation, by pulling the suture past the location of the cutter) or the cutter can be moved along the length of the suture. Alternatively, both the cutter and suture can be moved longitudinally, either in opposing directions or in the same direction at differing longitudinal speeds. The "net" velocity of longitudinal displacement (that is, the velocity at which the cutter and suture move longitudinally relative to one another) affects the pitch of the helical circumferential escarpment, and so may be varied to achieve the desired pitch: the greater the net longitudinal displacement velocity, the longer the helical pitch. It is to be understood that the displacer of this method can be either a single component effecting both longitudinal displacement and pivoting displacement or a combination of components to effect both types of displacement.

As the angle at which the cutter cuts into the suture (that is, the transverse cut angle) bears upon the direction in which the tissue retainer will face, the transverse cut angle can be an angle selected in the range between 90° and 180° relative to the longitudinal axis of the suture away from the suture deployment end that the retainer is to face; the transverse cut angle can typically be selected to be greater that 135° and less than 180° from the suture end that the retainer is to face, and can often be in the range of about 160° to about 170° from the suture deployment end. The greater the transverse cut angle, the deeper the cut creating the circumferential escarpment may be without eroding the integrity of the suture. Of course, as the transverse cut angle increases, the thickness of the resulting escarpment decreases, so the selection of the transverse cut angle may depend on the strength and/or resilience and/or rigidity of the suture material, the tissues for which the suture is intended, and so forth. Similarly, the selection of the depth of the circumferential cut may depend on factors including without limitation the aforementioned transverse cut angle, the diameter of the suture, and the tissues for which the suture is intended; exemplary parameters such as transverse cut angles, ratios of cut depth to suture diameter and cut distance to suture diameter and so forth are described in U.S. patent application Ser. No. 10/065,279, incorporated by reference. Where smaller retainer configurations are desired or larger suture diameters are present, a series of parallel helical cuts may be provided, as opposed to a single cut.

A step of cutting a second helical circumferential escarpment can be added to this method; such second helical escarpment may or may not intersect the first helical escarpment. The first and second helical escarpments may have the same or differing pitches (which depend on the rate of longitudinal displacement during the cutting of the escarpment) and cut depths, and/or the same or opposing chiralities. Depending upon the length of the escarpments and the respective transverse cut angles, a difference in pitch or chirality can result in intersection of the escarpments to create an escarpment point. The cutter can be, without limitation, a laser, a blade, a grinding wheel, or a cutting disc; the cutting surface can be abraded or "roughened" on one or both sides (as described in Section B above) to increase the surface area of one or both sides of the retainer. The cutter may be selected to cause the cut surfaces to disengage from one another, in order to facilitate engagement of the retainer with the tissue during affixation of the suture. Where a grinding wheel is selected as the cutter, the grinding action of the wheel removes some of the suture material in forming the escarpment and thereby increases the likelihood that the cut surfaces of the escarpment would disengage from one another during affixation. Further, where the cutter is a blade or cutting wheel, for example, it may be selected to have slightly thicker or wedge-shaped configuration to achieve this separation of cut surfaces. Cutting devices for cutting helical retainers and cutting fixtures for creating relative motion of cutting device and suture body to cut an escarpment in a helical pattern are described in more detail in Section F below.

Figure 4C:
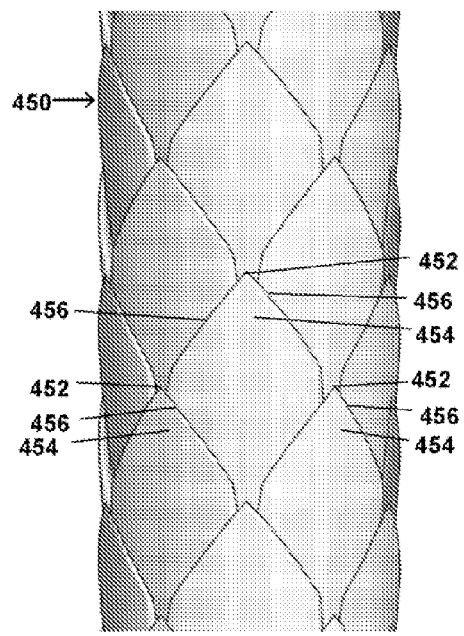
FIG. 4c is perspective view of an embodiment according to the present invention of a double helix self-retaining suture in an unexpanded position.
Figure 4D:
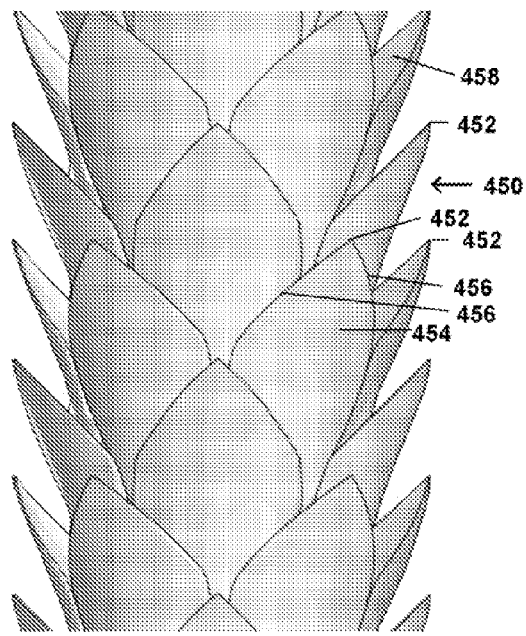
FIG. 4d is perspective view of an embodiment according to the present invention of a double helix self-retaining suture in an expanded position.

FIG. 4c discloses a scaled self-retaining suture 450 in an unexpanded position, produced by the foregoing method, wherein two intersecting helical escarpments are cut having substantially similar transverse cut angles, pitches, and cut depths, but opposing chiralities (i.e. the effect of combining 4a and 4b together). The resultant overlap of escarpment points 452 of suture 450 produces a pattern of scale-like retainers 454 having tissue-penetrating edges 456 and tissue-engaging surfaces 458; as the retainers 454 created by this method cover the entire circumferential suture surface on which they are cut, the tension on the suture 450 is optimally distributed and the risk of suture failure minimized. When such retainers 454 of suture 450 engage tissue, retainers 454 flare away from the suture body, as shown in the expanded position in FIG. 4d.

Figure 5:
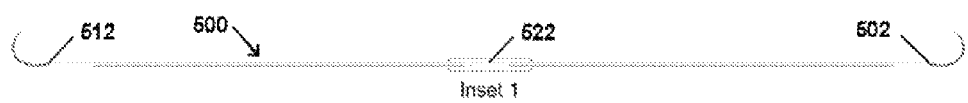
FIG. 5 is a perspective view of an embodiment according to the present invention of a bidirectional double helix self-retaining suture in an expanded position.
Figure 5:
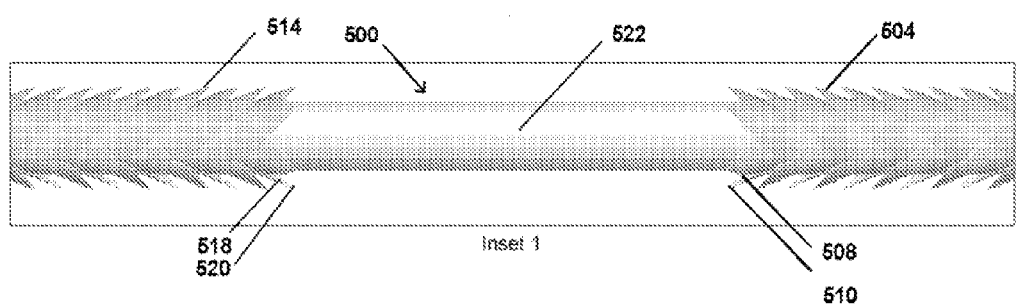

The foregoing steps may be carried out at the opposite end of the suture to create a bidirectional scaled self-retaining suture. For such a suture, a transition segment at some point between the ends of the suture is left retainer-free; the length of the transitional segment may be selected depending on the purpose of the suture, and the transitional segment may be located at or near the middle of the suture. Thus, to manufacture bidirectional scaled self-retaining sutures, the first pair of helical escarpments is cut along one end of the suture to a selected point some distance from the other suture end while the second pair of helical escarpments is cut to a selected point away from the first pair, so as to avoid having the first and second pair of escarpments from overlapping with one another and thereby providing a retainer-free transitional segment. For some bidirectional scaled self-retaining sutures, the orientation of one pair of helical escarpments at one end is about 180.degree. in orientation from the other pair of helical escarpments at the other end, thus creating an identical "mirrored" pattern of helical escarpments. Where smaller retainer configurations are desired or larger suture diameters are present, a series of parallel helical cuts may be provided, as opposed to a single cut. Both ends of the resulting bidirectional scaled self-retaining suture can function as suture deployment ends, and can therefore be adapted for attachment to deployment devices such as suture needles or for direct deployment into tissue without a deployment device. Referring now to FIG. 5, bidirectional scaled self-retaining suture 500 includes a first plurality of scale-like retainers 504 having retainer bodies 508 and tissue-penetrating edges 510 and a second plurality 514 of retainers 516 having retainer bodies 518 and tissue-penetrating edges 520. First retainer plurality 504 is disposed proximally to first suture deployment end 502, thus retainers 504 are oriented or pointed substantially away from end 502. Conversely, second retainer plurality 514 is disposed proximally to second suture deployment end 512, being accordingly oriented or pointed substantially away from end 512. First and second retainer pluralities 504 and 514 are separated by transition segment 522, that portion of a self-retaining bidirectional suture that is retainer-free.

Figure 6:
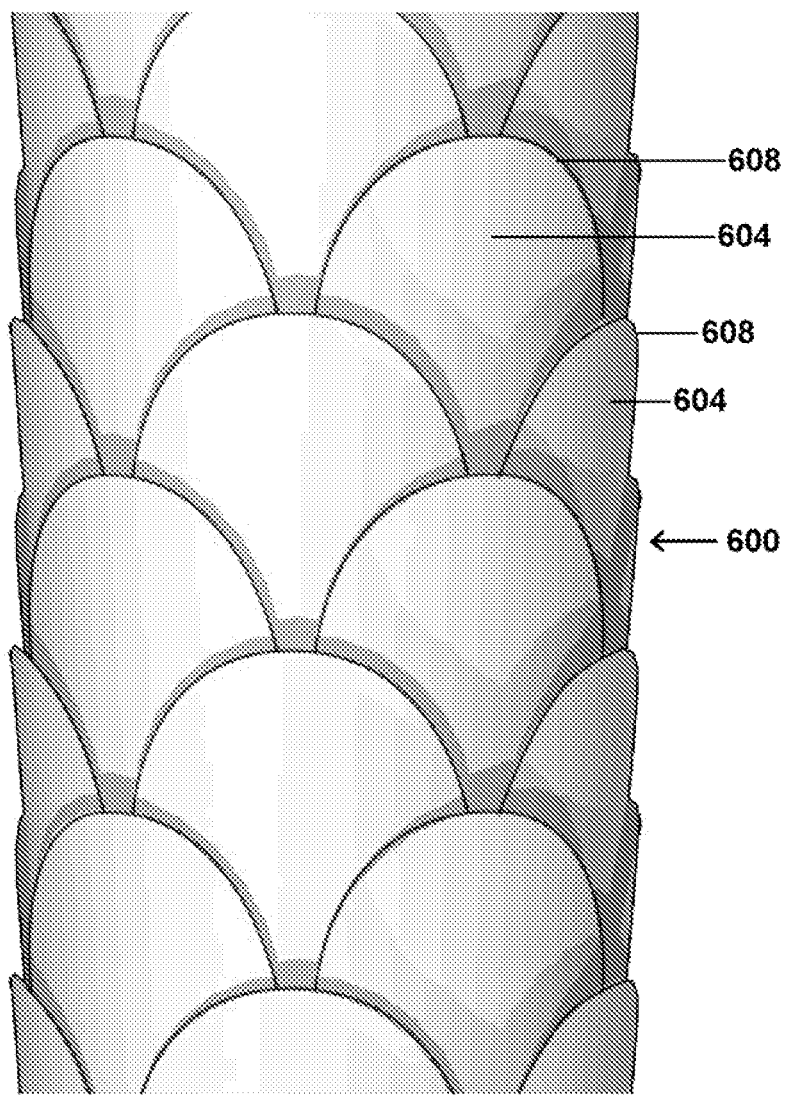
FIG. 6 is a perspective view of a further embodiment according to the present invention of a scaled self-retaining suture having rounded retainers.

If desired, a scaled self-retaining suture may be modified by rounding off or blunting the escarpment points. Referring now to FIG. 6, there is disclosed a scaled self-retaining suture 600 including on the suture body scale-like retainers 604 having retainer bodies 606 and tissue-penetrating edges 608. The tissue-penetrating edges 608 are rounded, producing a fish-scale effect, and are less likely bend or break without penetrating through and engaging the tissue. Similarly, a bidirectional self-retaining suture may be provided with rounded "scales", as shown in FIG. 7. Referring to that figure, bidirectional scaled self-retaining suture 700 (shown in the expanded position) includes a first plurality of scale-like retainers 704 having retainer bodies 708 and rounded tissue-penetrating edges 710 and a second plurality of retainers 714 having retainer bodies 718 and rounded tissue-penetrating edges 720. First retainer plurality 704 is disposed proximally to first suture deployment end 702, thus retainers 708 are oriented substantially away from end 702. Conversely, second retainer plurality 714 is disposed proximally to second suture deployment end 712, being separated from first retainer plurality 704 by transition segment 722, with retainers 718 being accordingly oriented substantially away from end 712.

The bidirectional sutures described herein may be further provided with an expanded transition segment for to further resist movement in tissue. Referring now to FIGS. 8a and 8b, bidirectional scaled self-retaining suture 800 (shown in the expanded position) includes a first plurality 804 of scale-like retainers 806 having retainer bodies 808 and tissue-penetrating edges 810 and a second plurality 814 of retainers 816 having retainer bodies 818 and tissue-penetrating edges 821. First retainer plurality 804 is disposed proximally to first suture deployment end 802, thus retainers 808 are oriented or pointed substantially away from end 802. Conversely, second retainer plurality 814 is disposed proximally to second suture deployment end 812, being separated from first retainer plurality 804 by transition segment 820, with retainers 818 being accordingly oriented or pointed substantially away from end 812. At transition segment 820, suture 800 has a greater diameter than at either end 802 or 812. As shown in this example, such expansion can be incremental, with the diameter increasing from each end 802 and 812 of suture 800 and reaching a maximum at transition segment 820; the incremental expansion may commence at a point outside the transitional segment, such that some part of the retainer-bearing portions of the suture thread may also have a greater diameter than that of a suture end.

In like fashion, the bidirectional scaled self-retaining suture 900 in FIGS. 9a and 9b (shown in the expanded position) includes a first plurality 904 of scale-like retainers 906 having retainer bodies 908 and rounded tissue-penetrating edges 910 and a second plurality 914 of retainers 916 having retainer bodies 918 and rounded tissue-penetrating edges 921. First retainer plurality 904 is disposed proximally to first suture deployment end 902, and the retainers 906 are oriented or pointed substantially away from end 902. Conversely, second retainer plurality 914 is disposed proximally to second suture deployment end 912, being separated from first retainer plurality 904 by transition segment 920. Retainers 918 are oriented or pointed substantially away from end 912. Suture 900 has a greater diameter at transition segment 920 than at either end 902 or 912. The expansion is shown in this example to be incremental, with the diameter increasing from each end 902 and 912 of suture 900 and reaching a maximum at transition segment 920; the incremental expansion may commence at a point outside the transitional segment, such that some part of the retainer-bearing portions of the suture thread may also have a greater diameter than that of a suture end.

Bidirectional scaled self-retaining sutures may further be provided with expanded diameter transitional segments as described in Section C herein, increased surface area provided by the tissue engagement surface configurations described in Section B, and secondary retainer structure configurations as described in Section E.

E. Secondary Retainer Structure Configurations

To further reduce issues of uneven tension distribution or insufficient tissue engagement from arising and potentially leading to suture failure, self-retaining sutures may be provided with a secondary retainer structure, that is, secondary retainers upon the primary retainers. Secondary retainers further increase the surface area of the suture and thereby increase the amount of interaction between the suture and tissue. Moreover, providing secondary retainers on the primary retainers increases the total number of retainers on the suture (and thus the total number of points of tissue penetration) without a reduction in suture tensile strength that may occur by cutting additional primary retainers into the suture body. The increase in the number of retainers and the increase in the suture's tissue engagement surface area results in better distribution of tension on the suture and increased tissue hold. FIGS. 6 through 8, inclusive, show self-retaining sutures having secondary retainers projecting from the primary retainers; the sutures can be unidirectional or bidirectional. In this connection, a self-retaining suture can include at least one primary retainer having a primary retainer body projecting from the suture body and a tissue penetrating end, and an inner surface substantially facing the suture body and an outer surface facing substantially away from the suture body, the primary retainer facing and deployed in a direction and being adapted for resisting movement of the suture when in tissue, in an opposite direction from the direction in which the primary retainer faces and is deployed. The primary retainer can further include at least one secondary retainer projecting from the primary retainer body. Such secondary retainers can be oriented in a direction at least about 90° away from the direction in which the primary retainer faces and is deployed, thus facilitating "double-hooking" of tissue, and may be located on any surface of the primary retainer. The primary retainer can be a barb, it can be frusto-conical, helical, and so forth. The secondary retainer can also be a barb, frusto-conical, helical, as well as filamentary.

Figure 10:
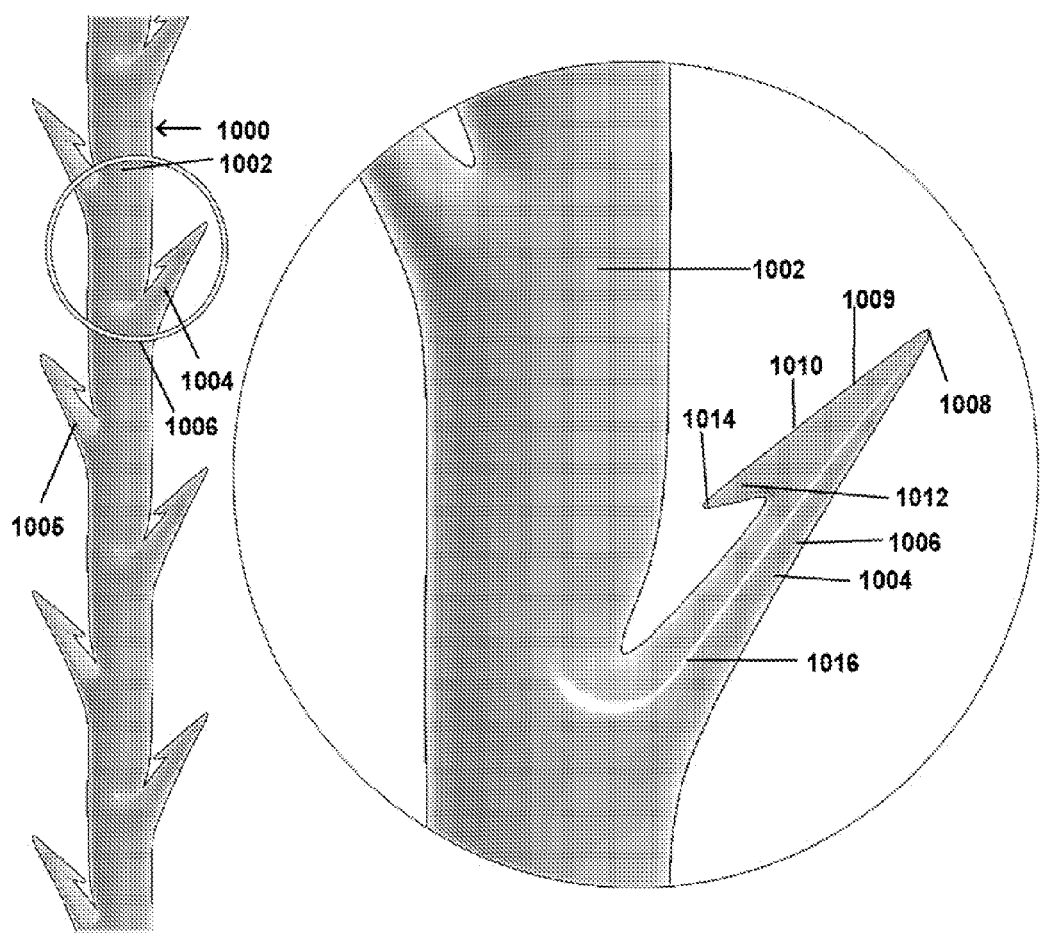
FIG. 10 is a perspective view of an embodiment according to the present invention of a self-retaining suture having a secondary retainer on a primary retainer.

Referring to FIG. 10, a self-retaining suture 1000 is shown, the suture 1000 including a suture body 1002 and a plurality of primary retainers 1004 with face 1005 extending from suture body 1002 and having primary retainer bodies 1006 and primary retainer edges 1008 and primary retainer tissue engagement surfaces 1016. The primary retainers 1004 further include a secondary retainer 1010 disposed on the tissue engagement surface 1016 at the primary retainer edge 1008 with face 1009 and with the primary retainer 1004 facing the deployment direction and with the second retainer 1010 facing substantially away from the deployment direction. The secondary retainers 1010 include a secondary retainer body 1012 and a secondary retainer edge 1014. Both primary and secondary retainers 1004 and 1010, respectively, are configured as barbs, such that the combination of the two have a "fishhook" appearance and function much the same way. That is, during suture deployment, primary retainers 1004 rest along suture body 1002 and secondary retainers 1010 in turn rest between primary retainers 1004 and suture body 1002. During affixation, primary retainers 1004 are displaced away from suture body 1002 thereby exposing secondary retainers 1010 and allowing them to further engage tissue being engaged between primary retainers 1004 and suture body 1002. Such a "fishhook" combination of primary and secondary retainers may be produced by forming a primary retainer on the suture thread by a single transverse cut and then removing some suture material from the tissue engagement surface of the retainer (such as by hand-cutting or laser-cutting) to form the secondary retainer. Alternatively, this combination may be made by making a first transverse cut on the suture thread to form the primary retainer, followed by back-cutting a second transverse cut onto the primary retainer to form the secondary retainer; these cuts may be made in a single continuous motion or may be made in separate motions. Similarly, the combination of primary retainers with "breakback" secondary retainers disposed on the tissue engagement surfaces of the primary retainers may be provided with frusto-conical and helical primary retainers; the secondary retainers may be cut onto the tissue engagement surfaces of such primary retainers to provide a secondary retainer lip along at least part of the length of the tissue penetrating edge of the primary retainer.

Figure 11:
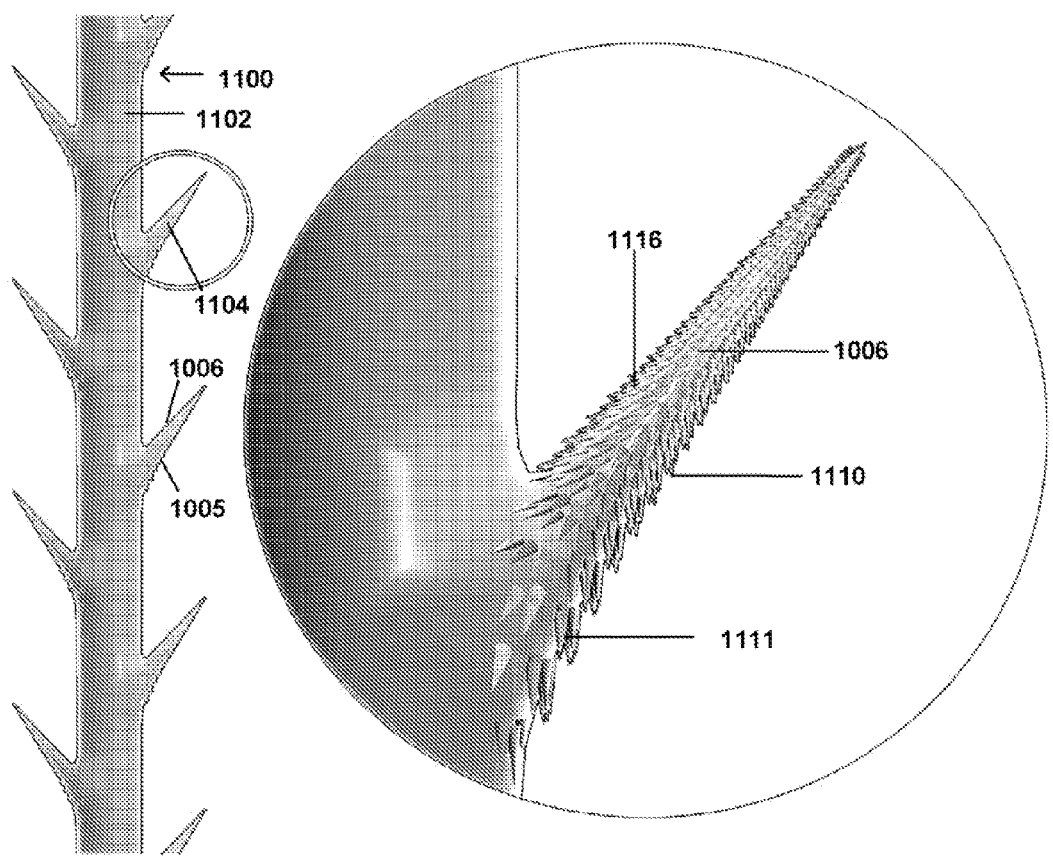
FIG. 11 is a perspective view of a further embodiment according to the present invention of a self-retaining suture having a plurality of secondary retainers on a primary retainer.

FIG. 11 discloses a primary/secondary retainer combination as well, but with a plurality of secondary retainers 1110 with face 1111 on primary retainer 1104 with face 1105. Thus, self-retaining suture 1100 includes suture body 1102 and primary retainers 1104 having a plurality of secondary retainers 1110 projecting from primary retainer body 1106 and with the secondary retainer 1110 located between the primary retainer 1104 and the suture body 1102 facing away from the direction of deployment Both primary and secondary retainers 1104 and 1110, respectively, are configured as barbs, such that the combination of the two resemble the microstructure of a porcupine's quill and function in much the same way. That is, during suture deployment, primary retainers 1104 rest along suture body 1102 and secondary retainers 1110 disposed on inner surface 1116 in turn rest between primary retainers 1104 and suture body 1102. As secondary retainers 1110 on the surfaces of the primary retainers 1104 other than inner surface 1116 are exposed during suture deployment, tissue resistance during deployment may increase slightly. However, once the primary barbs 1104 are affixed, the secondary retainers 1110 can enhance the hold or positioning of the primary retainers 1104. In addition, the uneven primary retainer surface resulting from these secondary retainers 1110 may increase local tissue disruption and increase surface area, both of which can promote healing and fixation. It is to be understood that such pluralities of secondary retainers may be provided on frusto-conical and helical primary retainers as well.

Figure 12:
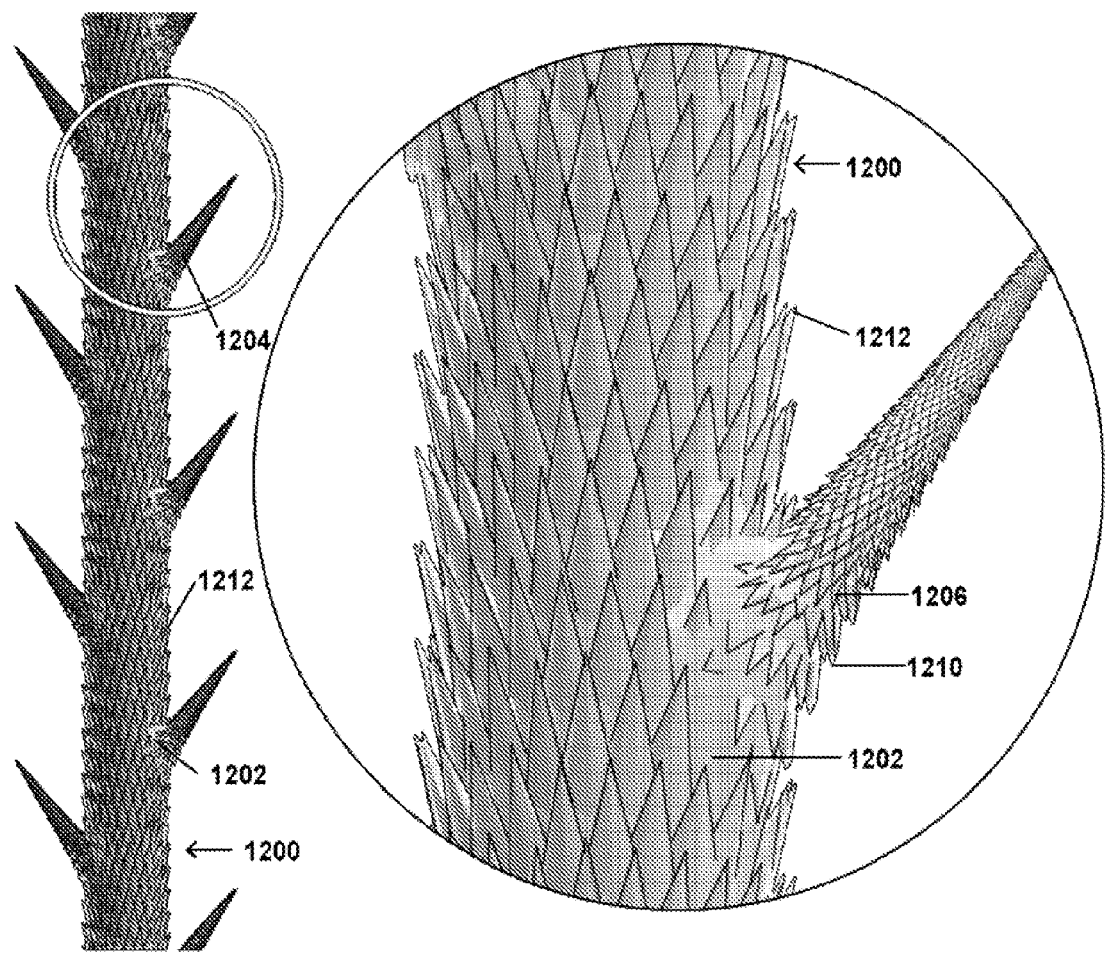
FIG. 12 is a perspective view of a further embodiment according to the present invention of a self-retaining suture having a plurality of secondary retainers on a primary retainer and secondary retainers on the body of the suture.

Self-retaining sutures having secondary retainers associated with primary retainers may further be provided with secondary retainers along the suture body, as disclosed in FIG. 12. Suture 1200 in FIG. 12 includes suture body 1202 and primary retainers 1204 having a plurality of secondary retainers 1210 (that project from primary retainer body 1206) and with the secondary retainer 1210 located between the primary retainer 1204 and the suture body 1202 facing away from the direction of deployment. Suture body 1202 further includes secondary retainers 1212, which point away from the direction of deployment and face the directly of deployment; given their orientation, secondary retainers 1212 rest along body 1202 during deployment of suture 1200 and so do not increase tissue resistance as suture 1200 is deployed through it. As do primary retainers 1204, secondary retainers 1212 fan away from suture body 1202 and engage tissue during affixation of the suture 1200. Provision of secondary retainers 1212 along suture body 1202 further increases surface area and therefore the holding strength of the suture. While retainers 1212 are configured as barbs, it is to be understood that other retainer configurations may be used.

Figure 13:
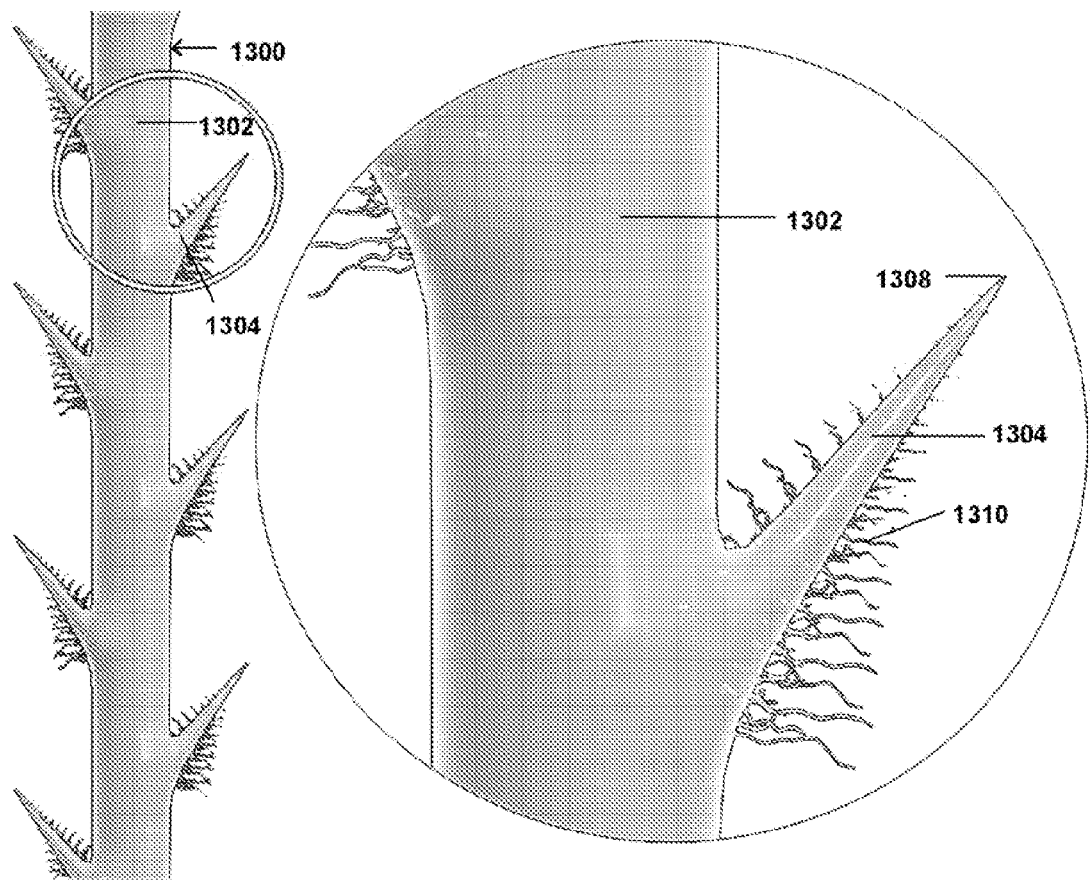
FIG. 13 is a perspective view of a further embodiment according to the present invention of a self-retaining suture having primary retainers and filamentary secondary retainers.

Yet another secondary retainer structure is illustrated in FIG. 13, which shows a self-retaining suture 1300 including a suture body 1302 and primary retainers 1304 having a plurality of secondary retainers 1310 extending from primary retainer bodies 1306, which secondary retainers 1310 are filamentary. These filamentary retainers 1310 may be created on the primary retainers 1304 by polymer grafting or growing techniques, by which polymer chains grown off of the surface of the primary retainers 1304 increase the microscopic surface area of the primary retainers 1304 thereby improving tissue engagement.

F. Manufacture of Self-Retaining Sutures

Suture threads described herein may be produced by any suitable method, including without limitation injection moulding, stamping, cutting, laser, extrusion, and so forth. With respect to cutting, polymeric thread or filaments may be manufactured or purchased for the suture body, and the retainers can be subsequently cut onto the suture body; they may be hand-cut, laser-cut, or mechanically machine-cut using blades, cutting wheels, grinding wheels, and so forth. The sutures may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

Figure 14A:
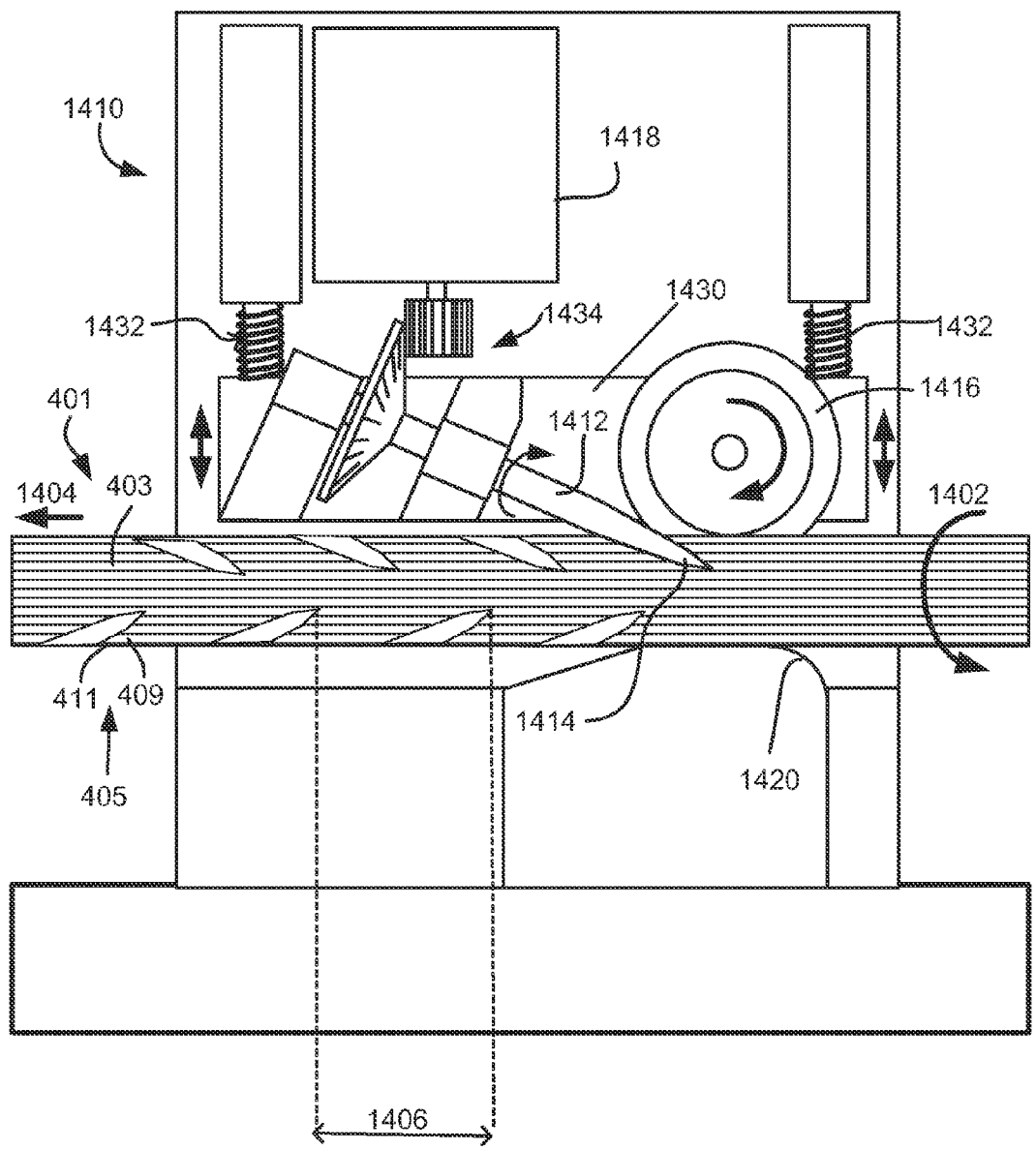
FIG. 14a is a partial cut away view of a cutting device for cutting a helical retainer in a suture body according to an embodiment of the present invention.

As described above, helical or spiral self-retaining sutures can be produced by a method including (i) providing a suture having a longitudinal axis and a circumference; a cutter; and, a displacer for longitudinally displacing and pivoting about the longitudinal axis at least one of the cutter and suture relative to one another; (ii) placing the cutter and suture into cutting engagement at a transverse cut angle; and, (iii) cutting a helical circumferential escarpment about the suture. FIG. 14a shows an embodiment of a cutting device for forming a helical retainer 405 disposed along a suture body 403 of a self-retaining suture 401, the helical retainer 405 including a retainer body 409 and a tissue penetrating edge 411.

As shown in FIG. 14a, a cutting device 1410 creates an escarpment in the surface of suture body 403. As shown in FIG. 14A the cutting device 1410 comprises, in one embodiment, a rotary cutting head 1412 can be, if desired, positioned adjacent suture body 403. Rotary cutting head is driven by motor 1418. Rotary cutting head 1412 is mounted such that the depth of tip 1414 of rotary cutting head 1412 is precisely controlled so that the depth of the escarpment is kept constant. In one embodiment, rotary cutting head may be held in fixed relationship with a roller 1416 which rides on suture body 403 thereby controlling the depth of the escarpment relative to the surface of the suture body 403. This allows for a constant escarpment depth even where the suture body varies in diameter. This is particular useful where the suture body has an expanded region of greater diameter as described above.

Roller 1416 and rotary cutting head 1412 are mounted to a floating armature 1430 which is pushed into contact with suture body 403 by springs 1432. The drive mechanism 1434 connecting motor 1418 and rotary cutting head 1412 allows movement of rotary cutting head 1412 without binding. Rotary cutting head 1412 is driven at a very high rotation rate compared to the translation and rotation of suture body 403. In alternative embodiments other cutting devices may be used including knives, abrasive wheels, lasers and the like. Alternative mechanisms may also be utilized to control the depth of cut including an electronically controlled sensor/servo system or other mechanical "following" systems. Where the diameter of suture body 403 is sufficiently uniform, the distance between roller 1416 and cutter support 1420 may be fixed rather than varying with the diameter of the suture body.

An anvil or cutter support 1420 is provided on the opposite side of suture body 403 from cutting device 1410 to support the suture body 403 during the cutting operation. The cutter support 1420 is designed to allow suture body 403 to translate longitudinally (arrow 1404) and rotate (arrow 1402) relative to cutting device 1410 but not to move laterally or vertically while passing through cutting device 1410. Cutter support 1420 thus maintains suture body 403 in the correct alignment with rotary cutting head 1412 during the cutting action. Suture body 403 is held between roller 1416 and cutter support 1420. Roller 1416 may also function to prevent lateral and vertical motion of suture body 403.

In order for cutting device 1410 to create a helical escarpment in the surface of suture body 403 one of cutting device 1410 or suture body 403 is rotated (arrow 1402) relative to the longitudinal axis of suture body 403 and translated (arrow 1404) along the longitudinal axis of suture body 403 at the same time. Alternatively, both suture body 403 and cutting device 1410 may be rotated about the longitudinal axis of the suture body 403, the suture body 403 being rotated while the cutting device 1410 revolves. In the latter case, suture body 403 and cutting device 1410 may be rotated either in the same direction or in opposing directions about the longitudinal axis of suture body 403. If both cutting device 1410 and suture body 403 are rotated in the same direction, the angular velocity at which each is rotated about the longitudinal axis must differ in order to effect a circumferential escarpment on the suture.

The speed of translation compared to the relative rate of rotation of cutting device 1410 and suture body 403 controls the pitch of the helical retainer 405. The pitch of the helical retainer 405 is the distance between turns. The pitch of helical retainer 405 is shown in FIG. 14a as dimension 1406. The faster the translation for a given rotation, the larger the pitch. Conversely, the faster the relative rotation for a given translational speed, the smaller the pitch. In some embodiments, the translation velocity and the rotational velocity will have a fixed relationship along the length of the suture body 403. However, in other embodiments it may be desirable for the pitch of the helical escarpment to be larger in some regions of the suture 401 than in others. This may be achieved by altering either or both of the relative rate of rotation and speed of translation during the passage of the suture body 403 through the cutting device 1410.

In order to form a helical retainer, a mechanism is used to generate the desired rate of rotation and speed of translation of the suture body 403 relative to the cutting device 1410.

Figure 14B:
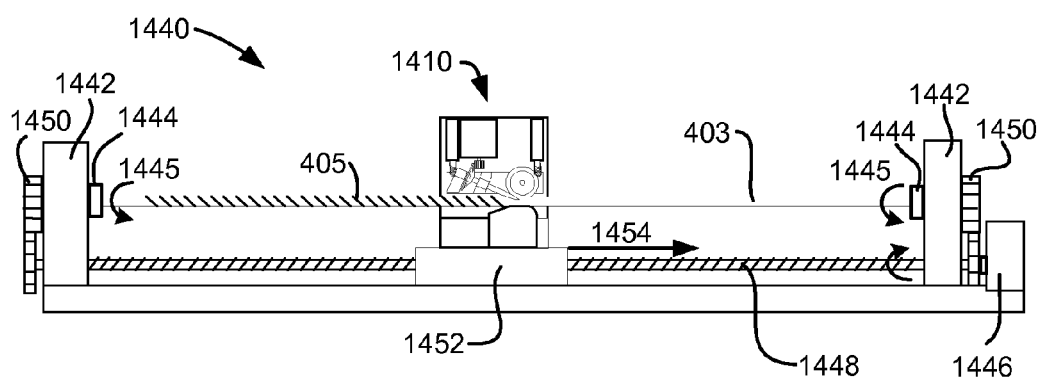
FIGS. 14b-14f are plan views of cutting fixtures for providing relative helical motion between a cutting device and a suture body according to embodiments of the present invention.

FIG. 14b shows one embodiment of a cutting fixture 1440 for forming a helical retainer 405 disposed along a suture body 403 of a self-retaining suture 401. Cutting fixture 1440 includes cutting device 1410 along with a mechanism for rotating suture body 403 and translating cutting device 1410 along suture body 403. As shown in FIG. 14b, suture body 403 is tensioned between two supports 1442. Suture body 403 is held to each support 1442 by a gear driven chuck 1444. A drive mechanism 1446, which may be an electric motor, drives a screw drive 1448 which runs between the supports 1442. Gears 1450 at each end of screw drive 1448 rotate chucks 1444 at the same speed and in the same direction as shown by arrows 1445. Screw drive 1448 also passes through a threaded passage in the base 1452 of cutting device 1410. As screw drive 1448 turns, screw drive 1448 drives cutting device 1410 linearly along the length of suture body 403 as shown by arrow 1454. Thus in cutting fixture 1440, suture body 403 is rotated relative to cutting device 1410 and cutting device 1410 is translated relative to suture body 403 thereby cutting a helical retainer 405 on suture body 403. Note that gears 1450 fix the ratio of translation speed of cutting device 1410 compared to the rate of rotation of suture body 403. Cutting fixture 1440 will, therefore, produce a helical retainer 405 with a constant pitch. Gears 1450 may be changed in order to change the pitch. Alternatively, if a variable pitch is desired, a separate drive mechanism 1446 may be provided for the chucks 1444 thereby allowing the rate of rotation of suture body 403 to be varied independent of the rate of translation of cutting device 1410. For example chucks 1446 and screw drive 1548 may be driven by separate computer-controlled electric drive systems.

Figure 14C:
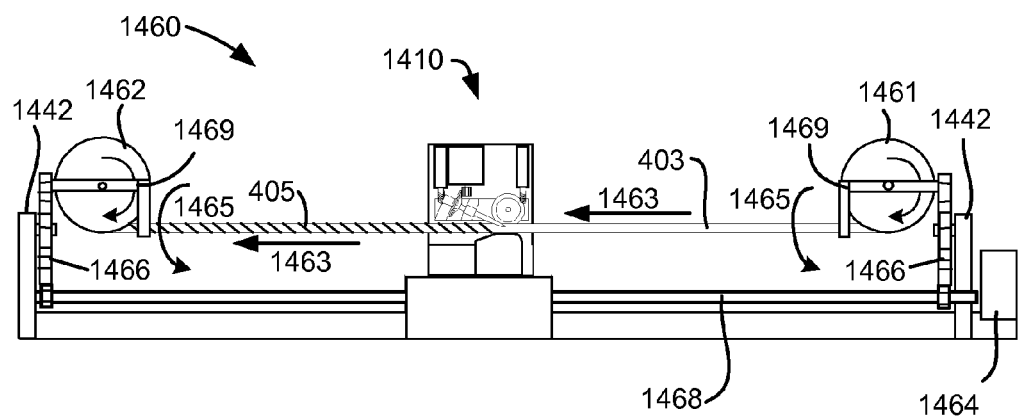

FIG. 14c shows an alternative cutting fixture 1460 for forming a helical retainer 405 disposed along a suture body 403 of a self-retaining suture 401. Cutting fixture 1460 includes cutting device 1410 along with a mechanism for rotating suture body 403 and translating suture body 403 relative to cutting device 1410. As shown in FIG. 14c, suture body 403 is tensioned between two supports 1442. Suture body 403 is held to each support 1442 by a feed spool 1461 or uptake spool 1462. Spools 1461 and 1462 rotate about their axes in the same speed and direction such that as the suture body 403 is played out by feed spool 1461 it is taken up uptake spool 1462 translating suture body 403 in the direction of arrows 1463. A mechanical tensioning mechanism (not shown) may also be provided to help maintain a constant tension in suture body 403 during the cutting process and to take up any slack cause by slight variation in the rate of suture play out and take up. A linear drive mechanism such as a screw drive may be used to translate suture body 403 as an alternative to drums or spools 1461, 1462. A drive mechanism 1464 drives shaft 1468 which runs between the supports 1442. Gears 1466 at each end of shaft 1468 rotate gimbles 1469 which hold spools 1461, 1462 to supports 1442. The gimbles 1469 rotate the spools 1461, 1462 about the longitudinal axis of suture body 403 as shown by arrows 1465. Thus, in cutting fixture 1460, suture body 403 is rotated and translated relative to a fixed-position cutting device 1410 thereby cutting a helical retainer 405 on suture body 403. If a variable pitch is desired, a separate drive mechanism 1466 may be provided for the rotation of the spools 1461, 1462 than the drive mechanism 1464 for shaft 1468 and gimbles 1469, thereby allowing the rate of rotation of suture body 403 to be varied independent of the rate of suture body 403.

FIG. 14c shows an alternative cutting fixture 1460 for forming a helical retainer 405 disposed along a suture body 403 of a self-retaining suture 401. Cutting fixture 1460 includes cutting device 1410 along with a mechanism for rotating suture body 403 and translating suture body 403 relative to cutting device 1410. As shown in FIG. 14c, suture body 403 is tensioned between two supports 1442. Suture body 403 is held to each support 1442 by a feed spool 1461 or uptake spool 1462. Spools 1461 and 1462 rotate about their axes in the same speed and direction such that as the suture body 403 is played out by feed spool 1461 it is taken up uptake spool 1462 translating suture body 403 in the direction of arrows 1463. A mechanical tensioning mechanism (not shown) may also be provided to help maintain a constant tension in suture body 403 during the cutting process and to take up any slack cause by slight variation in the rate of suture play out and take up. A linear drive mechanism such as a screw drive may be used to translate suture body 403 as an alternative to drums or spools 1461, 1462. A drive mechanism 1464 drives shaft 1468 which runs between the supports 1442. Gears 1466 at each end of shaft 1468 rotate gimbles 1469 which hold spools 1461, 1462 to supports 1442. The gimbles 1469 rotate the spools 1461, 1462 about the longitudinal axis of suture body 403 as shown by arrows 1465. Thus, in cutting fixture 1460, suture body 403 is rotated and translated relative to a fixed-position cutting device 1410 thereby cutting a helical retainer 405 on suture body 403. If a variable pitch is desired, a separate drive mechanism 1466 may be provided for the rotation of the spools 1461, 1462 than the drive mechanism 1464 for shaft 1468 and gimbles 1469, thereby allowing the rate of rotation of suture body 403 to be varied independent of the rate of suture body 403.

Figure 14D:
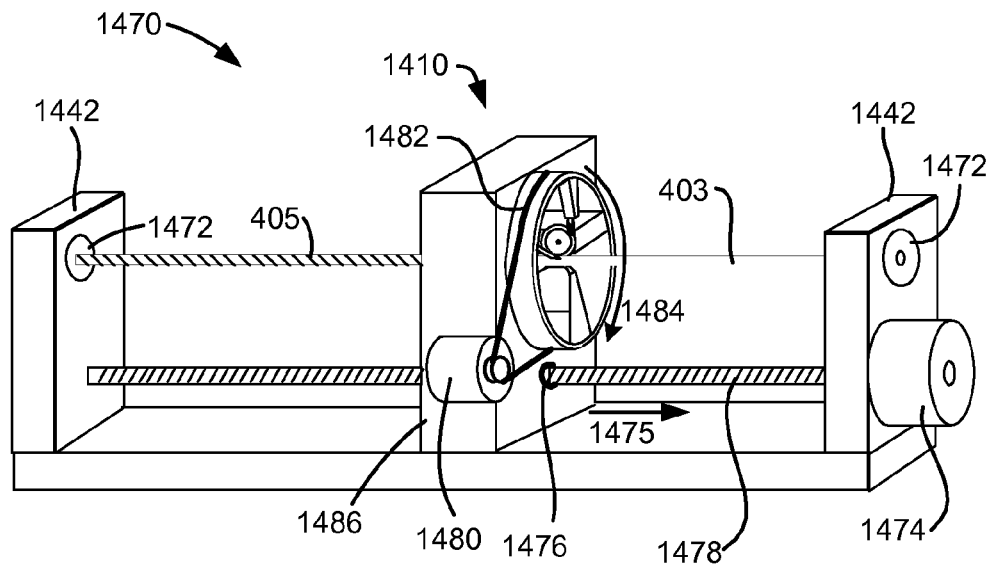
Figure 14E:
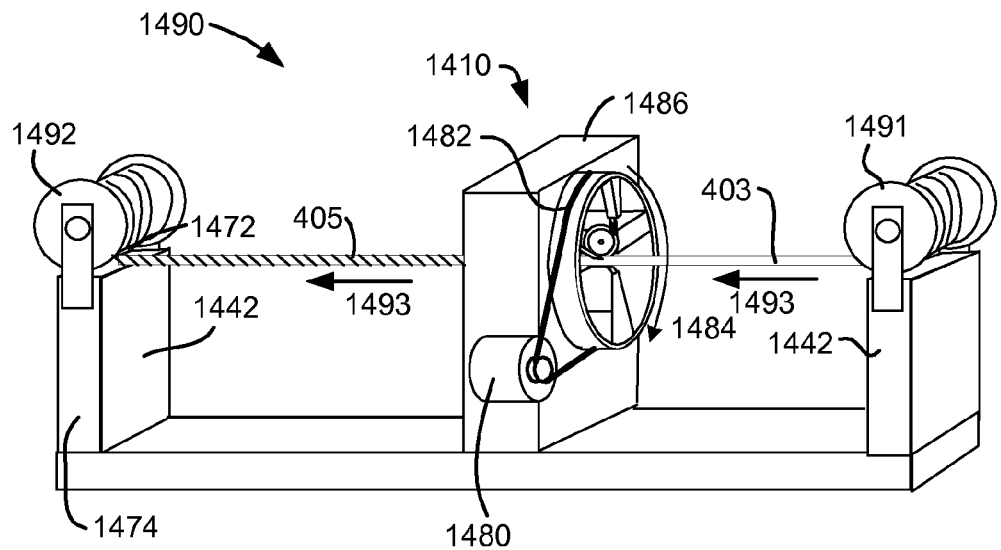

FIG. 14e shows an alternative cutting fixture 1490 for forming a helical or spiral retainer 405 disposed along a suture body 403 of a self-retaining suture. Cutting fixture 1490 includes cutting device 1410 along with a mechanism for rotating cutting device 1410 relative to suture body 403 and translating suture body 403 relative to cutting device 1410. As shown in FIG. 14e, suture body 403 is tensioned between two spools 1491, 1492. Feed spool 1491 and uptake spool 1492 rotate about their axes in the same speed and direction such that as the suture body 403 is played out by spool 1491 it is taken up spool 1492 translating suture body 403 in the direction of arrows 1493. A tensioning mechanism (not shown) may also be provided to help maintain a constant tension in suture body 403 during the cutting process and to take up any slack cause by slight variation in the rate of suture play out and take up. A linear drive mechanism such as a screw drive may be used to translate suture body 403 as an alternative to spools 1491, 1492. As with cutting fixture 1470 of FIG. 14d, a drive mechanism 1480 drives a belt 1482 which rotates cutting device 1410 within base 1486 as shown by arrow 1484. However, in cutting fixture 1490 base 1486 is stationary while suture body 403 translates. Thus in cutting fixture 1490, suture body 403 translates relative to cutting device 1410 and cutting device 1410 rotates relative to suture body 403 thereby cutting a helical retainer 405 on suture body 403. The pitch of helical retainer 405 may be controlled in this embodiment by adjusting the relative speeds of drive mechanism 1480 and spools 1491, 1492. If a fixed pitch is desired, a gear linkage may be used to drive spools 1491, 1492 from drive mechanism 1480. Alternatively separate drive mechanisms may be used and electronically controlled to maintain constant or varying rotational and translational speeds to create the constant of varying pitch desired.

Still alternatively, the mechanisms of FIG. 14c and FIG. 14e can be combined if it is desired to have the cutter revolve or rotate about the suture, and translate or be displaced along the longitudinal length of the suture in combination with having the suture both translate or be displaced along the longitudinal length, as well rotate or revolve about the axis of said suture. To accomplish this functionality the mechanism that longitudinally displaces or translates, and rotates the suture, which includes for example, the spools and gimbles and gears in FIG. 14c would replace the fixed chuck of FIG. 14d. Additionally, the mechanisms of FIG. 14b and FIG. 14e can be combined, if it is desired, to have the cutter revolve or rotate about the suture and translate or be displaced along the longitudinal length of the suture, in combination with the suture being rotated about the axis of the suture. To accomplish this functionality, the driven chucks of FIG. 14b would replace the fixed chucks of FIG. 14d. Alternatively to have the suture translate longitudinally and be in combination with having the cutter revolve or rotate and translate, the suture translation mechanism of FIG. 14e can be added to the device of FIG. 14d. Thus, the fixed chucks of FIG. 14d that hold the suture can be replaced in FIG. 14d with the spools of FIG. 14e so that the suture can translate or be displaced longitudinally.

Figure 14F:
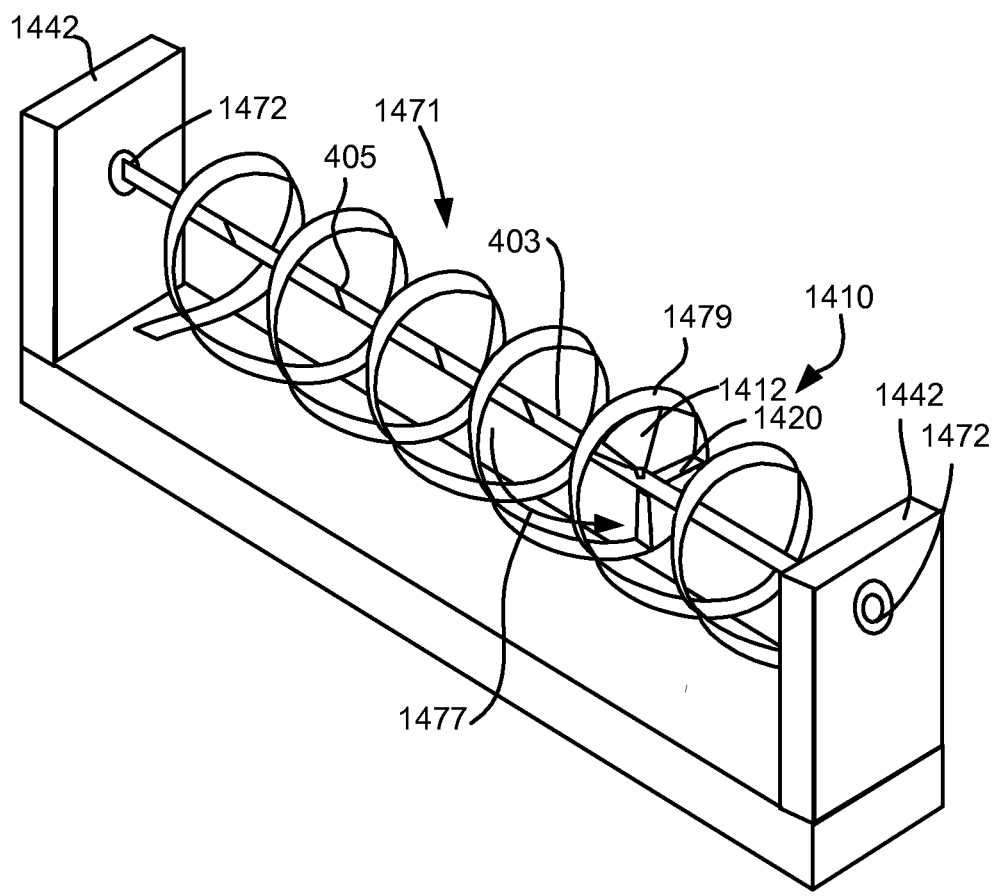

As, shown in FIG. 14f, as an alternative embodiment, the cutter rotating or revolving and cutter translating mechanism of FIG. 14d can be replaced with a spiral track or cylinder having an interior helical track that the cutter can be moved on. FIG. 14f shows an alternative cutting fixture 1471 for forming a helical retainer 405 disposed along a suture body 403 of a self-retaining suture 401. Cutting fixture 1471 includes cutting device 1410 along with a mechanism for rotating cutting device 1410 and translating cutting device 1410 relative to suture body 403. As shown in FIG. 14f, suture body 403 is tensioned between two supports 1442. Suture body 403 is held to each support 1442 by a fixed chuck 1472. A tensioning mechanism (not shown) may also be provided to help maintain a constant tension in suture body 403 during the cutting process. Cutting device 1410 which includes a cutting head 1412 and a cutter support 1420 travels along a helical track 1479 as shown by arrow 1477. In cutting fixture 1471 the cutting device 1410 is thereby moved along a helical path relative to the fixed suture body 403. Thus, in cutting fixture 1471, suture body 403 remains in a fixed position and cutting device 1410 is rotated and translated relative to suture body 403 thereby cutting a helical retainer 405 on suture body 403. The pitch of helical retainer 405 is fixed by the pitch of helical track 1479. As the cutting device 1410 is moved on the helical or spiral track, a helical or spiral cut is made on the suture body 403. It is to be noted that use of a helical track or a cylinder with an interior helical or spiral track can be made with any of the other embodiments herein, if it is desired, to have the cutter both rotate or revolve about the suture and have the cutter translate along the length of the suture. Still further, if desired in any of these embodiments, the suture can itself be pre-twisted prior to being loaded into any of the fixtures described.

Figure 15A:
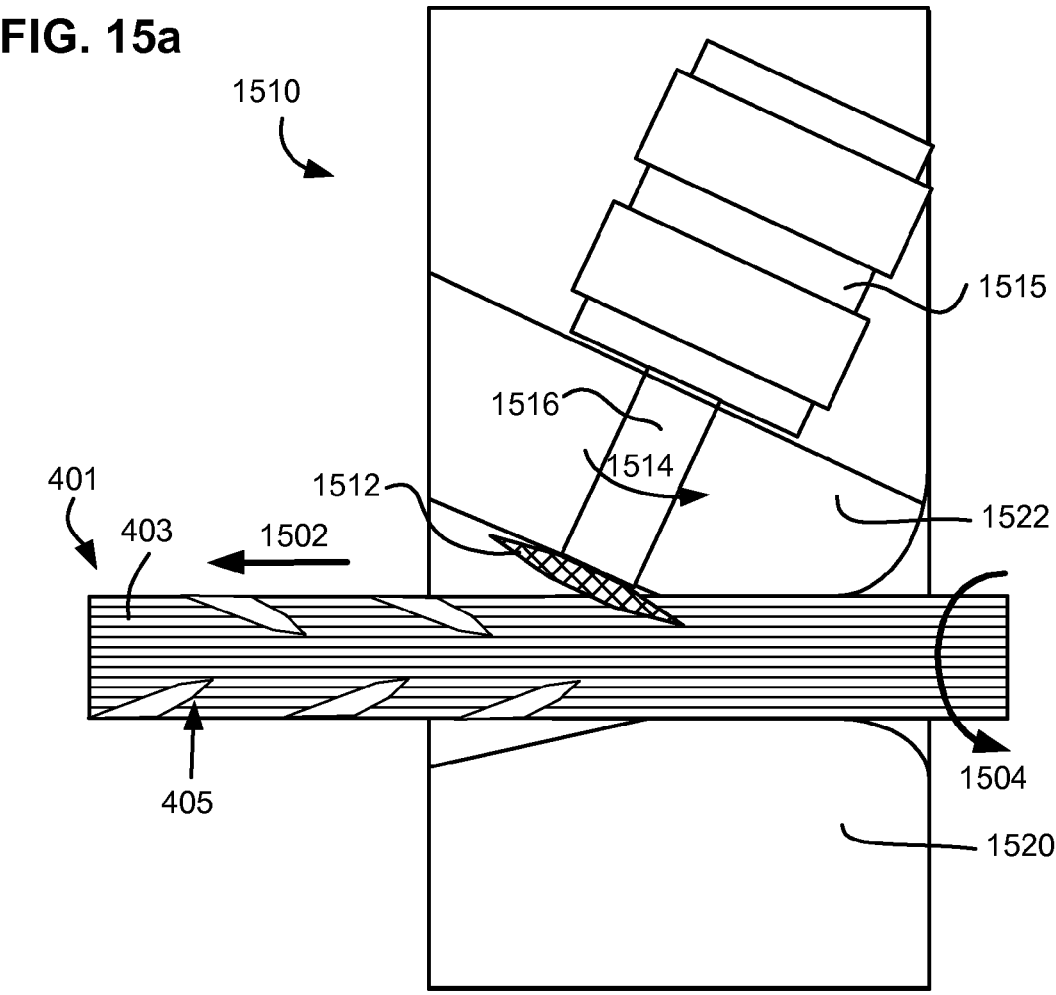
FIGS. 15a-15b are side and end views of an alternative cutting device according to embodiments of the present invention.

FIG. 15a shows an alternative cutting device 1510 that may be used in the cutting fixtures of FIGS. 14b-14f. As shown in FIG. 15a the suture body 403 passes between cutter support 1520 and support 1522. A rotary cutting blade 1512 rotates as shown by arrow 1514. Rotary cutting blade 1512 is mounted on shaft 1516 which passes through support 1522. The geometry of rotary cutting blade 1512 is thereby fixed relative to suture body 403. It may, however, be desirable to provide set screws or the like in order to adjust the angle and depth of the rotary cutting blade 1512 relative to the suture body 403. Rotary cutting blade may be a knife blade in which case the rotation of the blade may be either passive or driven. The knife blade made of a suitable ceramic or metal material for cutting into suture body 403. If the rotation is passive, rotary cutting blade 1512 turns in response to the rotation of suture body 403 against rotary cutting blade 1512. If the rotation of rotary cutting blade 1512 is driven, rotary cutting blade 1512 is driven by motor 1515. Rotary cutting blade 1512 may be an abrasive wheel or the like in which case rotary cutting blade 1512 is preferably driven at high speed or very high speed relative to the rotation of suture body 403. If the rotation of rotary cutting blade 1512 is driven, it may be driven in the same direction as suture body 403 or in the opposite direction. Rotary cutting blade 1512 is moved along a helical path relative to suture body 403 utilizing a cutting fixture which provides for relative translation and rotation of cutting device 1510 and the suture body 403 as shown by arrows 1502 and 1504 respectively. Suitable cutting fixtures are described with respect to FIGS. 14b-14f above. As described above, either or both of cutting device 1510 and suture body 403 may be moved in order to generate the desired helical path of the cutting device 1510 about the suture body 403.

Figure 15B:
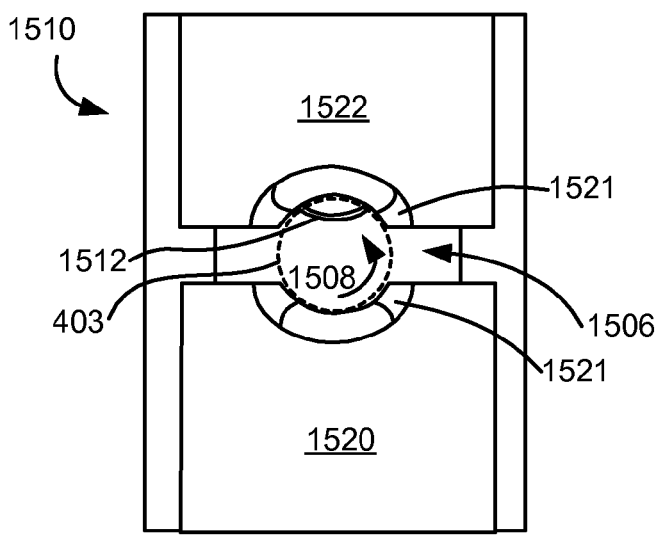

FIG. 15b shows an end view of cutting device 1510 illustrating the entrance aperture 1506 into cutting device 1510. Entrance aperture 1506 into cutting device 1510 is defined by the space between supports 1520 and 1522. Supports 1520 and 1522 are each provided with a polished radius or polished chamfer 1521 to guide suture body 403 (position shown by dashed line) into aperture 1506 without abrading suture body 403. Rotary cutting blade 1512 can seen protruding into aperture 1506 adjacent support 1521. In alternative embodiments a plurality of cutting blades may be provide in order to cut a plurality of helical retainers at the same time. As suture body 403 enters aperture 1506 (into the page) suture body 403 rotates in the direction of arrow 1508 relative to cutting device. 1510. Note that either the suture body 403 or the cutting device 1510 may be rotated to achieve the desired relative rotation of cutting device 1510 and suture body 403.

Figure 15C:
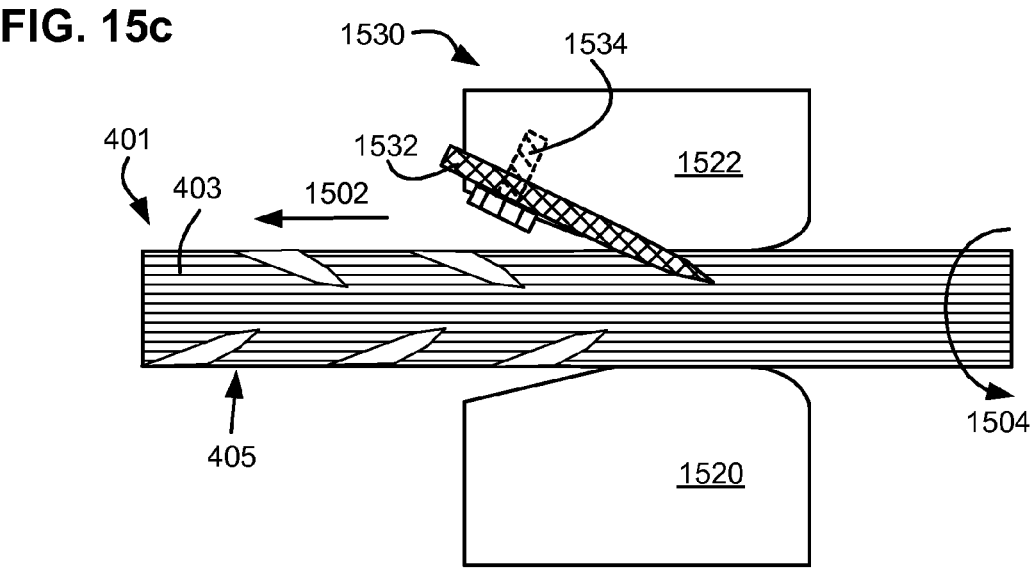
FIG. 15c is a side view of an alternative cutting device according to an embodiment of the present invention.

FIG. 15c shows another alternative cutting device 1530 that may be used in the cutting fixtures of FIGS. 14b-14f. As shown in FIG. 15a the suture body 403 passes between cutter support 1520 and support 1522. A fixed cutting blade 1532 is mounted to support 1522 by machine screw 1534. Machine screw 1534 allows the position of cutting blade 1532 to be adjusted relative to suture body 403. It may be desirable to provide further set screws or the like in order to better adjust the angle and depth of the rotary cutting blade 1512 relative to the suture body 403. Cutting blade may be a knife blade made of a suitable ceramic or metal material for cutting into suture body 403. Cutting blade 1532 is moved along a helical path relative to suture body 403 utilizing a cutting fixture which provides for relative translation and rotation of cutting device 1510 and the suture body 403 as shown by arrows 1502 and 1504 respectively. Suitable cutting fixtures are described with respect to FIGS. 14b-14f above. As described above, either or both of cutting device 1510 and suture body 403 may be moved in order to generate the desired helical path of the cutting device 1510 about the suture body 403.

Self-retaining sutures described herein may also incorporate materials that further promote tissue engagement. In addition to tissue engagement at the retainers, use of tissue engagement-promoting materials in at least part of the suture bodies (whether or not such materials also make up all or part of the retainers) can enhance the ability of the sutures to stay in place. One such class of tissue engagement-promoting materials are porous polymers that can be extruded to form suture bodies, including both microporous polymers and polymers that can be extruded with bubbles (whether bioabsorbable or nonbioabsorbable). A suture synthesized with such materials can have a three-dimensional lattice structure that increases tissue engagement surface area and permits tissue infiltration into the suture body itself, thus having a primary structure that promotes successful suture use. Moreover, by optimizing pore size, fibroblast ingrowth can be encouraged, further facilitating the suture to be anchored in the tissue.

One such microporous polymer is ePTFE (expanded polytetra-fluoroethylene). Self-retaining incorporating ePTFE (and related microporous materials) are well-suited to uses requiring a strong and permanent lift (such as breast lifts, face lifts, and other tissue repositioning procedures), as tissue infiltration of the suture results in improved fixation and engraftment of the suture and the surrounding tissue thus providing superior hold and greater longevity of the lift.

Additionally, self-retaining sutures described herein may be provided with compositions to promote healing and prevent undesirable effects such as scar formation, infection, pain, and so forth. This can be accomplished in a variety of manners, including for example: (a) by directly affixing to the suture a formulation (e.g., by either spraying the suture with a polymer/drug film, or by dipping the suture into a polymer/drug solution), (b) by coating the suture with a substance such as a hydrogel which will in turn absorb the composition, (c) by interweaving formulation-coated thread (or the polymer itself formed into a thread) into the suture structure in the case of multi-filamentary sutures, (d) by inserting the suture into a sleeve or mesh which is comprised of, or coated with, a formulation, or (e) constructing the suture itself with a composition. Such compositions may include without limitation anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents. For example, a composition can be applied to the suture before the retainers are formed, so that when the retainers engage, the engaging surface is substantially free of the coating. In this way, tissue being sutured contacts a coated surface of the suture as the suture is introduced, but when the retainer engages, a non-coated surface of the retainer contacts the tissue. Alternatively, the suture may be coated after or during formation of retainers on the suture if, for example, a fully-coated rather than selectively-coated suture is desired. In yet another alternative, a suture may be selectively coated either during or after formation of retainers by exposing only selected portions of the suture to the coating. The particular purpose to which the suture is to be put or the composition may determine whether a fully-coated or selectively-coated suture is appropriate; for example, with lubricious coatings, it may be desirable to selectively coat the suture, leaving, for instance, the tissue-engaging surfaces of the sutures uncoated in order to prevent the tissue engagement function of those surfaces from being impaired. On the other hand, coatings such as those comprising such compounds as anti-infective agents may suitably be applied to the entire suture, while coatings such as those comprising fibrosing agents may suitably be applied to all or part of the suture (such as the tissue-engaging surfaces). The purpose of the suture may also determine the sort of coating that is applied to the suture; for example, self-retaining sutures having anti-proliferative coatings may be used in closing tumour excision sites, while self-retaining sutures with fibrosing coatings may be used in tissue repositioning procedures and those having anti-scarring coatings may be used for wound closure on the skin. As well, the structure of the suture may influence the choice and extent of coating; for example, sutures having an expanded segment may include a fibrosis-inducing composition on the expanded segment to further secure the segment in position in the tissue. Coatings may also include a plurality of compositions either together or on different portions of the suture, where the multiple compositions can be selected either for different purposes (such as combinations of analgesics, anti-infective and anti-scarring agents) or for their synergistic effects.

G. Clinical Uses

In addition to the general wound closure and soft tissue repair applications described in the preceding sections, self retaining sutures can be used in a variety of other indications.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0 or USP 10-0, and may have an attached needle of corresponding size. They may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber.

Self retaining sutures can be used in a variety of veterinary applications for a wide number of surgical and traumatic purposes in animal health.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A method of forming retainers on a suture, said method comprising: providing a suture having a longitudinal axis and a circumference; providing a cutter; providing a displacer including a track that can longitudinally displace at least one of the suture and the cutter relative to the other, and can at least one of revolve the cutter about the suture and rotate the suture; placing the cutter and suture into cutting engagement to form a first helical escarpment about the suture circumference; rotating the cutter about a cutter axis; and moving the cutter along the track.

2. The method of claim 1, further comprising cutting a second helical escarpment.

3. The method of claim 2, comprising cutting the second escarpment to intersect the first escarpment at least one escarpment point.

4. The method of claim 3, further comprising the step of rounding off the at least one escarpment point.

5. The method of claim 2, comprising cutting the first and second escarpments to have differing pitches.

6. The method of claim 2, comprising cutting the first and second escarpments to be chirally opposing.

7. The method of claim 2, comprising cutting the first and second escarpments to have substantially similar cut depths.

8. The method of claim 7, comprising cutting the first and second escarpments proximal to an end of the suture.

9. The method of claim 2, comprising cutting the first and second escarpments to have differing cut depths.

10. The method of claim 1, comprising using the cutter selected from the class comprised of lasers, blades, grinding wheels, and cutting discs.

11. The method of claim 1, comprising providing on the suture a coating.

12. The method of claim 11, comprising providing a coating that comprises at least one composition selected from the class consisting of anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents.

13. The method of claim 1, comprising providing a coating on the suture that comprises at least in part in at least one composition selected from the class consisting of anti-proliferative agents, anti-angiogenic agents, anti-infective agents, fibrosis-inducing agents, anti-scarring agents, lubricious agents, echogenic agents, anti-inflammatory agents, cell cycle inhibitors, analgesics, and anti-microtubule agents.

14. The method of claim 1 wherein the placing step includes placing the cutter and the suture into cutting engagement at a transverse cut angle; and the step of cutting at a cut angle to form the first helical escarpment about the suture circumference.

15. The method of claim 1 wherein the step of providing a displacer comprises both the cutter revolving and the suture rotating relative to the other.

16. The method of claim 1 wherein the step of providing a displacer comprises selectively one of the cutters revolving and the suture rotating relative to the other.

17. The method of claim 1 wherein said suture providing step includes providing a twisted suture.

18. The method of claim 1 wherein said displacer moves the track along the longitudinal axis.

19. An apparatus to form a retainer on a suture comprising: a suture holding frame adapted to hold a suture along a longitudinal axis; a cutter that can cut the retainer; and a displacer that can (1) displace at least one of the suture holding frame, the suture in the suture holding frame and the cutter along the longitudinal axis, (2) rotate the suture holding frame, and (3) can at least one of revolve the cutter about the suture, and rotate the suture.

20. The apparatus of claim 19 comprising: a placer that can place the cutter in cutting engagement with the suture in order to cut the retainer.

21. The apparatus of claim 19 comprising a cutter rotating motor engaged with the cutter to rotate the cutter about a cutter axis.

22. The apparatus of claim 19 wherein said displacer includes, in said suture holding frame, a suture feeding mechanism that is adapted to move the suture along the longitudinal axis.

23. The apparatus of claim 19 wherein said displacer includes a spiraling track, and can revolve said cutter along the spiraling track.

24. An apparatus to form a retainer on a suture comprising: a suture holding frame adapted to hold a suture along a longitudinal axis; a cutter that can cut the retainer; and a displacer that can (1) displace at least one of the suture holding frame, the suture in the suture holding frame and the cutter along the longitudinal axis, and (2) can at least one of revolve the cutter about the suture, and rotate the suture; and wherein said displacer includes a spiraling track, and can revolve said cutter along the spiraling track.

25. The apparatus of claim 24 comprising: a placer that can place the cutter in cutting engagement with the suture in order to cut the retainer.

26. The apparatus of claim 24 comprising a cutter rotating motor engaged with the cutter to rotate the cutter about a cutter axis.

27. The apparatus of claim 24 wherein said displacer includes, in said suture holding frame, a suture feeding mechanism that is adapted to move the suture along the longitudinal axis.

28. The apparatus of claim 24 wherein said displacer can rotate the suture holding frame.

* * * * *